United States Patent [19] — [11] 4,234,591
Akkerman et al. — [45] Nov. 18, 1980

[54] ANALGESIC AND MORPHINE-ANTAGONISTIC 9-PHENYL-6,7-BENZOMORPHANS

[75] Inventors: Antony M. Akkerman, Amsterdam; Hermanus C. C. K. Van Bakel, Montfoort; Henriette G. van Breevoort-Uurbanus, Nieuw-Loosdrecht, all of Netherlands

[73] Assignee: ACF Chemiefarma N.V., Maarssen, Netherlands

[21] Appl. No.: 36,089

[22] Filed: May 4, 1979

Related U.S. Application Data

[63] Continuation of Ser. No. 804,149, Jun. 6, 1977, abandoned.

[30] Foreign Application Priority Data

Jun. 21, 1976 [GB] United Kingdom ............... 25577/76

[51] Int. Cl.³ .................. A61K 31/445; C07D 221/26
[52] U.S. Cl. ...................................... 424/267; 546/97
[58] Field of Search ........................... 546/97; 424/267

[56] References Cited

U.S. PATENT DOCUMENTS

| 3,320,265 | 5/1967 | Clarke | 546/97 |
| 3,511,846 | 5/1970 | Munch | 546/97 |
| 3,639,407 | 2/1972 | Clarke et al. | 546/97 |
| 3,932,422 | 1/1976 | Michne | 546/97 X |

FOREIGN PATENT DOCUMENTS

| 45-31664 | 10/1970 | Japan | 546/97 |
| 1079489 | 8/1967 | United Kingdom | 546/97 |
| 1261481 | 1/1972 | United Kingdom | 546/97 |

OTHER PUBLICATIONS

Eddy, N., et al., *J. Org. Chem.*, 22, 1370 (1957).

*Primary Examiner*—Henry R. Jiles
*Assistant Examiner*—Richard A. Schwartz
*Attorney, Agent, or Firm*—Curtis, Morris & Safford

[57] ABSTRACT

The invention is concerned with certain new 6,7-benzomorphan derivatives having pharmacological, in particular analgesic and/or morphine-antagonistic properties, of the formula

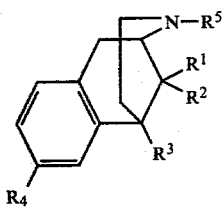

wherein $R^1$ is a substituted or unsubstituted phenyl or heteroaryl group; $R^2$ is a hydrogen or halogen atom, or a hydroxy, alkoxy or acyloxy group; $R^3$ is an alkyl or alkenyl group; $R^4$ is a hydrogen atom or a hydroxy, alkoxy or acyloxy group; and $R^5$ is an alkyl group or, when $R^2$ is hydrogen in a trans-position to $R^3$, $R^5$ is a hydrogen atom or an alkyl, alkenyl, alkinyl, cycloalkyl, cycloalkylalkyl, cycloalkenylalkyl, cyanoalkyl, hydroxyalkyl, alkoxyalkyl, or a substituted or unsubstituted phenylalkyl, heteroarylalkyl or heterocycloalkylalkyl group; optical isomers and pharmaceutically acceptable sals thereof.

The preferred compound is the α-isomer of 2,5-dimethyl- 2'-hydroxy-9-phenyl-6,7-benzomorphan, in particular its (+)-enantiomer.

These compounds are prepared by total synthesis and are not derived from opium alkaloids.

21 Claims, No Drawings

ANALGESIC AND MORPHINE-ANTAGONISTIC 9-PHENYL-6,7-BENZOMORPHANS

This is a continuation of application Ser. No. 804,149, filed June 6, 1977, now abandoned.

This invention is concerned with certain novel 6,7-benzomorphan derivatives, with methods for their preparation, and pharmaceutical compositions containing them.

Since 1955, when the first 6,7-benzomorphans with analgesic activity became known, viz 5,9-dialkyl-6,7--benzomorphans (E. L. May and J. G. Murphy, J. Org. Chem. 20, 257 (1955), many additional members of this tricyclic ring system have been described. A number of compounds of this type are analgesics, antagonists to analgesics or show a combination of these properties, depending mainly on the nature of the substituent at the 2-position, i.e. on the ring nitrogen atom. The activities may be considerable if a hydroxy group is present at the 2'-position.

Some 6,7-benzomorphans have been successfully used in medicine, see e.g. N. B. Eddy and E. L. May in "International Series of Monographs in Organic Chemistry", Vol. 8 Part II (B), Pergamon Press (1966); A. F. Casy in "Progress in Medical Chemistry", Vol. 7, 229 (1970), Butterworths; H. W. Kosterlitz, H. O. J. Collier and J. E. Villarreal in "Agonist and Antagonist actions of narcotic analgesic drugs", MacMillan (1972); M. C. Braude, L. S. Harris, E. L. May, J. P. Smith and J. E. Villarreal in "Narcotic antagonists", Advances in Biochemical Psychopharmacology, 8 (1973). Usually, these 6,7-benzomorphans possess a quaternary carbon atom at the 5-position, while the 9-position is either unsubstituted or substituted by one single methyl or ethyl group.

6,7-Benzomorphans with two quaternary carbon atoms, at the 5- and the 9-position, have been previously described, c.f. our British Pat. No. 1,299,699. 6,7-Benzomorphans with one quaternary carbon atom at the 9-position, bearing two alkyl groups, and no substituent at the 5-position are the subject of our British Patent Application No. 7891/75. As used herein, the expression "quaternary carbon atom" means a carbon atom having all four valencies bonded to carbon atoms not belonging to functional groups.

Other carbon substitution patterns at the 5- and 9-positions encountered in the 6,7-benzomorphan series are: an aryl substituent at C5, in combination with hydrogen or with one or two alkyl substituents at C9, see e.g. F. H. Clarke, R. T. Hill, J. K. Saelens and N. Yokoyama in "Advances in Biochemical Psychopharmacology" 8, 81 (1973) and British Pat. No. 1,299,669; an alkyl substituent at C9 and no substituent at the 5-position, see T. Oh-Ishi, A. E. Jacobson, R. S. Wilson, H. J. C. Yeh and E. L. May, J. Org. Chem. 39, 1347 (1974); H. Inoue, T. Oh-Ishi and E. L. May, J. Med. Chem. 18, 787 (1975); no substituents at the 5- and 9-positions, see K. Kanematsu, R. T. Parfitt, A. E. Jacobson, J. H. Ager and E. L. May, J. Am. Chem. Soc. 90, 1064 (1968), K. Kanematsu, M. Takeda, A. E. Jacobson and E. L. May, J. Med. Chem. 12, 405 (1969); M. Takeda, A. E. Jacobson, K. Kanematsu and E. L. May, J. Org. Chem. 34, 4154 (1969); K. Mitsuhasha, S. Shiotani, R. Oh-Uchi and H. Shiraki, Chem. Pharm. Bull. 17, 434 (1969); a hydroxy or an acyloxy substituent at the 5-position and no substituents at the 9-position, see M. Takeda and E. L. May, J. Med. Chem. 13, 1223 (1970); and a hydroxy or an acyloxy substituent at the 9-position, combined with an alkyl, aralkyl or alkenyl substituent at the 5-position, and hydrogen or a lower alkyl, alkenyl or alkinyl substituent at the other C9, see E. L. May et al., J. Org. Chem. 26, 188, 1621, 1954, 4536 (1961); J. Med. Chem. 8, 235 (1965); Dutch Patent Applications Nos. 73.14758, 74.09743 and 75.04648; German Patent Application No. 2.353.794; U.S. Pat. No. 3.853.889; J. Monkovic, Can. J. Chem. 53, 1189 (1975). There are few reports on further alternatives, e.g. concerning substitution at positions other than the above-mentioned 2-, 5- and 9-positions.

We have now found that certain new 6,7-benzomorphan derivatives with an aryl or heteroaryl substituent at the 9-position have pharmacological properties. These derivatives comprise compounds of the formula:

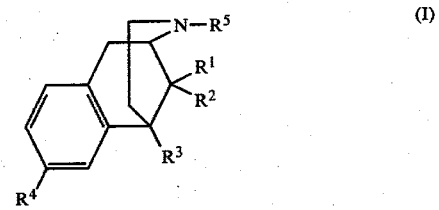

(I)

wherein $R^1$ is a substituted or unsubstituted phenyl or heteroaryl group; $R^2$ is a hydrogen or halogen atom, or a hydroxy, alkoxy or acyloxy group; $R^3$ is an alkyl or alkenyl group; $R^4$ is a hydrogen atom or a hydroxy, alkoxy or acyloxy group; and $R^5$ is an alkyl group or, when $R^2$ is hydrogen in a trans-position to $R^3$, $R^5$ is a hydrogen atom or an alkyl, alkenyl, alkinyl, cycloalkyl, cycloalkylalkyl, cycloalkenylalkyl, cyanoalkyl, hydroxyalkyl, alkoxyalkyl, or a substituted or unsubstituted phenylalkyl, heteroarylalkyl or heterocycloalkylalkyl group; optical isomers and pharmaceutically acceptable salts thereof.

These compounds and the said salts are novel and form one aspect of the present invention. They are collectively hereinafter referred to as "the compounds of the invention".

The invention also provides a pharmaceutical composition which comprises a compound of formula I or a pharmaceutically acceptable salt thereof, together with a pharmaceutically acceptable carrier or diluent therefor.

One sub-class of the compounds of the invention is that is which $R^1$, $R^2$, $R^3$, $R^4$ and $R^5$ are as defined above except that $R^5$ is not a hydroxyalkyl or a substituted phenylalkyl, heteroarylalkyl or heterocycloalkylalkyl group, and $R^1$ is not a substituted heteroaryl group.

In the compounds of the invention, $R^1$ is suitably, for example, phenyl, or phenyl substituted by halogen, alkyl, trifluoromethyl, hydroxy, alkoxy, disubstituted amino including piperidine or dialkylamino; or heteroaryl in which the hetero atom is sulphur or nitrogen, e.g. thienyl or pyridyl. Preferably, $R^1$ is phenyl, hydroxyphenyl, alkylphenyl or chlorophenyl. Most preferably, $R^1$ is an unsubstituted phenyl group.

$R^2$ is suitably, for example, hydrogen, hydroxy, methoxy, acetoxy or chlorine, preferably hydrogen.

$R^3$ is suitably, for example, methyl, ethyl, n-propyl, allyl or butenyl, preferably methyl.

$R^4$ is suitably, for example, hydrogen, hydroxy, methoxy, ethoxy, n-propoxy, lower alkanoyloxy (i.e. up to 4 carbon atom) for example acetoxy; phenylalkanoyloxy, alkylaroyloxy or nicotinoyloxy. Preferably, $R^4$ is hydroxy, methoxy or acetoxy, most preferably hydroxy.

$R^5$ is suitably, for example, hydrogen, methyl, ethyl, n-propyl, iso-propyl, n-, iso-, or sec.-butyl, n-hexyl, allyl, 3-methyl-2-butenyl, propargyl; cyclopentyl, cyclopropylmethyl or cyclobutylmethyl wherein the cycloalkyl group may be substituted by one or two alkyl groups, cyclohexenylmethyl, cyanopropyl, 2-hydroxy-2-methylpropyl, 2-hydroxypropyl, methoxyethyl, 3-methoxypropyl, ethoxyethyl, 2-methoxy-2-methylpropyl, 2-methoxypropyl, phenethyl, p-methoxyphenethyl, p-chlorophenethyl, p-nitrophenethyl, heteroarylalkyl preferably containing an oxygen atom such as furfuryl and 3-furylmethyl wherein the furyl group may be substituted by one or more alkyl groups, heterocycloalkylalkyl preferably containing one or two oxygen atoms such as tetrahydrofurfuryl. Preferably, $R^5$ is methyl, ethyl, n-butyl, allyl, methoxyethyl, methoxypropyl, ethoxyethyl, phenethyl, p-methoxyphenylethyl, cyclopropylmethyl or tetrahydrofurfuryl. Most preferably, $R^5$ is methyl, ethyl, methoxyethyl, ethoxyethyl or p-methoxyphenylethyl.

It will be appreciated that the compounds of the invention contain the basic 6,7-benzomorphan nucleus, their plane formula being:

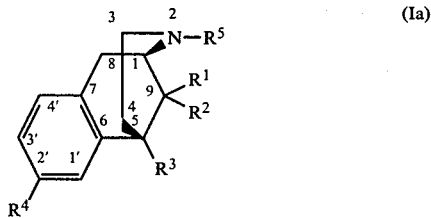

Whilst the carbon atoms at positions 1, 5 and 9 are all asymmetric, only two diastereoisomeric forms are possible because the iminoethano bridge between C1 and C5 is constrained to a cis (1,3-diaxial) configuration. Hence, the diastereoisomers can only differ in the configuration at C9, where $R^1$ and $R^2$ may each be either cis or trans to the iminoethano bridge. In accordance with convention, when $R^1$ is trans to the bridge (and, therefore, cis to $R^3$), the isomer is called an α-isomer. When $R^1$ is cis to the bridge (and hence trans to $R^3$) the isomer is called a β-isomer.

The α- and β-isomers can in theory each exist in two optical isomeric forms, namely the laevorotatory and dextrorotatory enantiomers, and the inventions includes all the isomers of formula I and salts thereof, mixtures of two or more such isomers, and the individual isomers in their resolvent form. The graphic representations herein include the dl racemic mixtures and the resolved d- and l-isomers thereof.

The pharmacological properties of the compounds of the invention vary depending on the nature of the substituents, $R^1$, $R^2$, $R^3$, $R^4$ and $R^5$. The compounds may possess analgesic activity or morphine-antagonistic activity, or a combination of these two activities. Those compounds showing the combined properties can be considered as analgesics with a lower chance of development of tolerance and addiction than the known morphine-like drugs.

The pharmacological activity of the compounds of the invention also varies with the nature of the substituents, $R^1$, $R^2$, $R^3$, $R^4$ and $R^5$. Thus, some compounds will have a greater pharmacological activity than others.

Among the compounds which are preferred in this respect are those (including the enantiomers and pharmaceutically acceptable acid addition salts) in which $R^1$ and $R^3$ are cis to one another, and (a) $R^1$ is phenyl, $R^2$ is hydrogen and $R^4$ is hydroxy or methoxy;

(b) $R^1$ is phenyl, $R^2$ is hydrogen, $R^3$ is alkyl and $R^4$ is hydroxy or methoxy;

(c) $R^1$ is phenyl, $R^2$ is hydrogen, $R^3$ is alkyl, $R^4$ is hydroxy or methoxy and $R^5$ is methyl;

(d) $R^1$ is phenyl, $R^2$ is hydrogen, $R^3$ is alkyl, $R^4$ is hydroxy and $R^5$ is methyl;

(e) $R^1$ is phenyl, $R^2$ is hydrogen, $R^3$ is methyl, $R^4$ is hydroxy and $R^5$ is methyl, particularly the (+)-enantiomer;

(f) $R^1$ is phenyl, $R^2$ is hydrogen, $R^3$ is ethyl, $R^4$ is hydroxy and $R^5$ is methyl;

(g) $R^1$ is phenyl, $R^2$ is hydrogen, $R^3$ is n-propyl, $R^4$ is hydroxy and $R^5$ is methyl;

(h) $R^1$ is phenyl, $R^2$ is hydrogen, $R^3$ is allyl, $R^4$ is hydroxy and $R^5$ is methyl;

(i) $R^1$ is phenyl, $R^2$ is hydrogen, $R^3$ is methyl, ethyl or n-propyl, $R^4$ is methoxy and $R^5$ is methyl;

(j) $R^1$ is o-tolyl or m-hydroxyphenyl, $R^2$ is hydrogen, $R^3$ is methyl, $R^4$ is hydroxy and $R^5$ is methyl;

(k) $R^1$ is phenyl, $R^2$ is hydrogen, $R^3$ is methyl, $R^4$ is hydroxy and $R^5$ is ethyl, methoxyethyl, ethoxyethyl or p-methoxyphenethyl;

(l) $R^1$ is phenyl, $R^2$ is hydrogen, $R^3$ is methyl, $R^4$ is hydroxy and $R^5$ is tetrahydrofurfuryl, phenethyl, allyl, n-butyl, cyclopropylmethyl or methoxypropyl;

(m) $R^1$ is phenyl, $R^2$ is hydrogen, $R^3$ is methyl, $R^4$ is hydroxy and $R^5$ is hydroxyalkyl;

(n) $R^1$ is phenyl, $R^2$ is hydrogen, $R^3$ is methyl, $R^4$ is hydroxy and $R^5$ is 2-hydroxy-2-methylpropyl; and (o) $R^1$ is phenyl, $R^2$ is hydrogen, $R^3$ is ethyl, $R^4$ is hydroxy and $R^5$ is ethyl or methoxyethyl.

Those compounds of the invention which are particularly useful as intermediates in the manufacture of other compounds of the invention include 2',9-dihydroxy-2,5-dimethyl-9-phenyl-6,7-benzomorphan (both diastereoisomers), 9-chloro-2,5-dimethyl-2'-hydroxy-9-phenyl-6,7-benzomorphan, 9-chloro-2,5-dimethyl-2'-methoxy-9-phenyl-6,7-benzomorphan, 2,5-dimethyl-9-hydroxy-2'-methoxy-9-phenyl-6,7-benzomorphan (both diastereoisomers), 2,5-dimethyl-2'-methoxy-9-phenyl-6,7-benzomorphan (preferably α-isomer), 2'-methoxy-5-methyl-9-phenyl-6,7-benzomorphan (α-isomer), 2'-hydroxy-5-methyl-9-phenyl-6,7-benzomorphan (α-isomer), and the corresponding 5-ethyl compounds.

The compounds of the invention can be made in various ways. The invention includes a process for preparing a benzomorphan derivative of formula I (a) which comprises converting one derivative of formula I into another derivative of formula I by one or more steps;

(b) wherein $R^1$ and $R^3$ are as defined in formula I, except that $R^1$ is not hydroxyphenyl or hydroxyheteroaryl, $R^2$ is hydroxy, $R^4$ is hydrogen or alkoxy and $R^5$ is alkyl, which comprises reacting a compound of the formula:

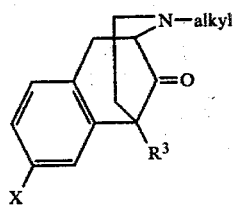

II wherein $R^3$ is as defined in formula I and X is hydrogen or alkoxy, with an organometallic compound to produce a compound of the formula:

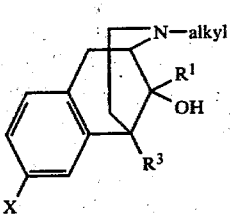

III wherein $R^1$ is as defined in formula I but is not hydroxyphenyl or hydroxyheteroaryl, and $R^3$ and X are unchanged;

(c) which comprises converting a compound of formula III above into another compound of the invention by one or more steps;

(d) wherein $R^2$ is hydrogen, $R^5$ is alkyl and $R^1$, $R^3$ and $R^4$ are as defined in formula I, except that $R^3$ is not alkenyl, or wherein $R^2$ is halogen, $R^4$ is hydrogen or alkoxy, $R^5$ is alkyl and $R^1$ and $R^3$ are as defined in formula I except that $R^1$ is not hydroxyphenyl or hydroxyheteroaryl, and $R^3$ is not alkenyl, which comprises treating a compound of formula

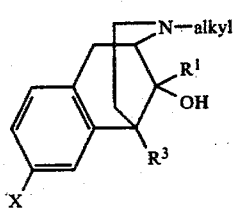

III wherein $R^1$ and $R^3$ are as defined in claim 1 except that $R^1$ is not hydroxyphenyl or hydroxyheteroaryl and $R^3$ is not an alkenyl group, and X is hydrogen or alkoxy, with a halogenating agent to form a compound of the formula

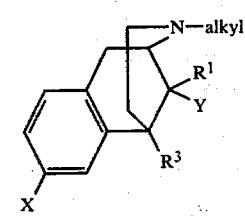

IV wherein $R^1$, $R^3$ and X are unchanged and Y is halogen, preferably chlorine;

and, if desired, reducing the compound of formula IV to produce a compound of formula

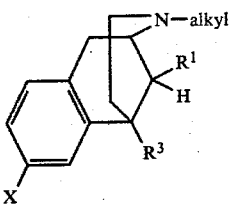

V wherein $R^1$, $R^2$ and X are unchanged;

and, if desired, cleaving the aromatic ether function of the compound of formula V wherein X is alkoxy, to produce the corresponding 2′-hydroxy compound of formula

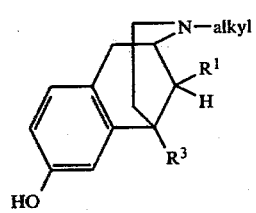

XV wherein $R^1$ and $R^3$ are as defined in claim 1 except that $R^1$ is not alkoxyphenyl or alkoxyheteroaryl and $R^3$ is not an alkenyl group;

and, if desired, converting the compound of formula XV into a compound of formula

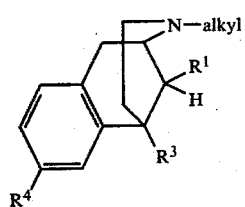

XVII wherein $R^4$ is alkoxy or acyloxy, $R^1$ and $R_3$ are as defined in formula I except that $R^1$ is not hydroxyphenyl or hydroxyheteroaryl and $R^3$ is not alkenyl;

(e) wherein $R^5$ is alkyl, $R^2$ is hydrogen, $R^1$, $R^2$ and $R^4$ are as defined in formula I, which comprises reducing a compound of formula

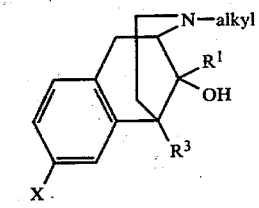

III wherein $R^1$ and $R^3$ are cis relative to each other and are otherwise as defined in claim 1 except that $R^1$ is not hydroxyphenyl or hydroxyheteroaryl, and X is hydrogen or alkoxy, with lithium and liquid ammonia to produce a compound of the formula

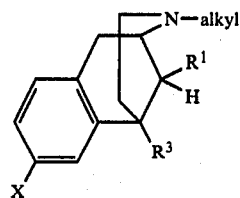

wherein X, $R^1$ and $R^3$ are as defined above;
and, if desired, cleaving the aromatic ether function of the compound of formula V wherein X is alkoxy, to produce the corresponding 2'-hydroxy compound of formula

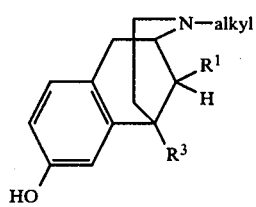

wherein $R^1$ and $R^3$ are as defined in claim 1 except that $R^1$ is not alkoxyphenyl or alkoxyheteroaryl;
and, if desired, converting the compound of formula XV into a compound of form

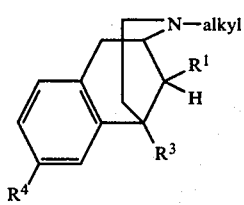

wherein $R^4$ is alkoxy or acyloxy, $R^1$ and $R^3$ are as defined in formula I except that $R^1$ is not hydroxyphenyl or hydroxyheteroaryl;
(f) wherein $R^5$ is alkyl, $R^2$ and $R^4$ are hydroxy and $R^1$ and $R^3$ are as defined in formula I except that $R^1$ is not alkoxyphenyl or alkoxyheteroaryl, which comprises ether splitting a compound of formula

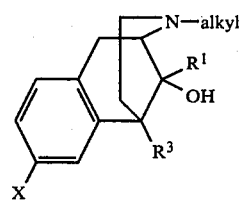

wherein $R^1$ and $R^3$ are as defined in formula I except that $R^1$ is not hydroxyphenyl or hydroxyheteroaryl and X is alkoxy, to produce a compound of formula

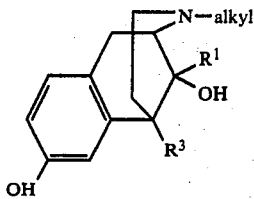

wherein $R^1$ and $R^3$ are as defined in formula I except that $R^1$ is not alkoxyphenyl or alkoxyheteroaryl;
(g) wherein $R^5$ is alkyl, $R^4$ is hydroxy, $R^2$ is halogen and $R^1$ and $R^3$ are as defined in formula I except that $R^1$ is not alkoxyphenyl or alkoxyheteroaryl, and $R^3$ is not alkenyl, or wherein $R^5$ is alkyl, $R^4$ is as defined in formula I other than hydrogen, $R^3$ is as defined in claim 1 other than alkenyl, $R^2$ is hydrogen and $R^1$ is as defined in claim 1, which comprises treating a compound of formula VIII (see above), wherein $R^1$ and $R^3$ are as defined in formula I except that $R^1$ is not alkoxyphenyl or alkoxyheteroaryl and $R^3$ is not alkenyl, with a halogenating agent to form a compound of the formula

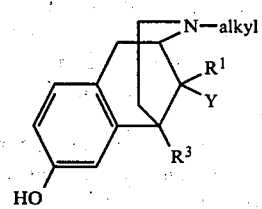

wherein Y is halogen and $R^1$ and $R^3$ are unchanged;
and, if desired, reducing the compound of formula XX to produce a compound of the formula

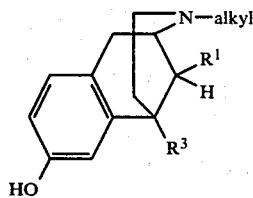

wherein $R^1$ and $R^3$ are unchanged;
and, if desired, converting the compound of formula XV to a compound of formula

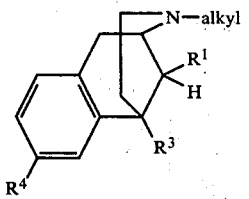

wherein $R^1$ is as defined in formula I except that $R^1$ is not hydroxyphenyl or hydroxyheteroaryl, $R^3$ is unchanged and $R^4$ is alkoxy or acyloxy;
(h) wherein $R^5$ is alkyl, $R^4$ is hydroxy, $R^3$ is as defined in formula I other than alkenyl, $R^2$ is halogen and $R^1$ is as defined in formula I other than alkoxyphenyl or alkoxyheteroaryl, or wherein $R^5$ and $R^3$ are as above stated, $R^4$ is as defined in formula I other than hydrogen, $R^2$ is hydrogen and $R^1$ is as defined in formula I, which comprises ether splitting a compound of the formula

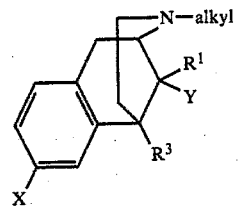   IV wherein X is alkoxy, Y is halogen, $R^1$ is as defined in formula I other than hydroxyphenyl or hydroxyheteroaryl, and $R^3$ is as above stated, to form a compound of the formula

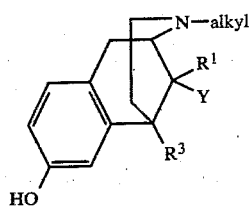   XX wherein $R^3$ and Y are unchanged and $R^1$ is as defined in formula I other than alkoxyphenyl or alkoxyheteroaryl;

and, if desired, reducing the compound of formula XX to produce a compound of the formula

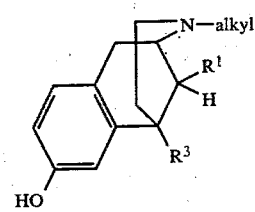   XV wherein $R^1$ and $R^3$ are unchanged;

and, if desired, converting the compound of formula XV to a compound of formula

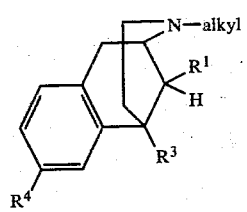   XVII wherein $R^1$ is as defined in formula I except that $R^1$ is not hydroxyphenyl or hydroxyheteroaryl, $R^3$ is unchanged and $R^4$ is alkoxy or acyloxy;

(i) wherein $R^1$, $R^3$, $R^4$ and $R^5$ are as defined in formula I except that $R^1$ and $R^3$ are cis relative to each other, and $R^2$ is hydrogen, which comprises N-dealkylating a compound of the formula

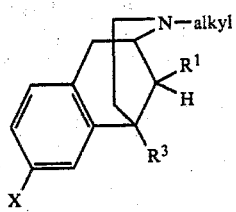   V wherein $R^1$ and $R^3$ are as above stated except that $R^1$ is not hydroxyphenyl or hydroxyheteroaryl, and X is hydrogen or alkoxy, to produce a compound of the formula

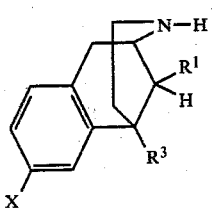   XII wherein $R^1$, $R^3$ and X are unchanged;

and, if desired, introducing a $R^5$ substituent to form a compound of the formula

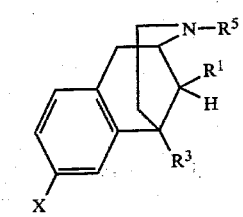   XIII wherein $R^1$, $R^3$ and X are unchanged, and $R^5$ is as defined in formula I other than hydrogen;

and, if desired, cleaving the aromatic ether function of the compound of formula XII or XIII wherein X is alkoxy to form a compound of the formula

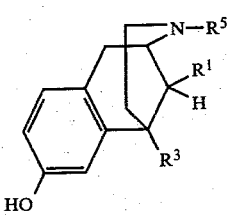   XIV wherein $R^1$ and $R^3$ are as above stated except that $R^1$ is not alkoxyphenyl or alkoxyheteroaryl and $R^5$ is as defined in formula I;

and, if desired, converting the compound of formula XIV to the compound of formula

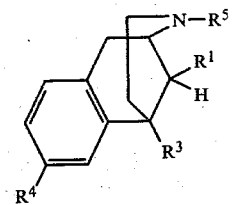   XVI wherein $R^1$ and $R^3$ are as above stated except that $R^1$ is not hydroxyphenyl or hydroxyheteroaryl, $R^4$ is alkoxy or acyloxy and $R^5$ is as defined in formula I;

(j) wherein $R^1$, $R^3$ and $R^5$ are as defined in formula I except that $R^1$ and $R^3$ are cis relative to each other, $R^2$ is hydrogen, and $R^4$ is hydroxy, alkoxy or acyloxy except that when $R^5$ is hydrogen, $R^4$ is hydroxy, which comprises ether splitting a compound of the formula

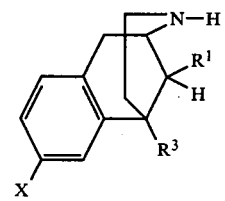

XII wherein X is alkoxy and $R^1$ and $R^3$ are as stated above, except that $R^1$ is not hydroxyphenyl or hydroxyheteroaryl,
to form a compound of formula

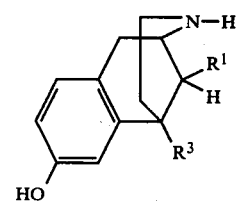

XIIa wherein $R^1$ and $R^3$ are as stated above, except that $R^1$ is not alkoxyphenyl or alkoxyheteroaryl;
and, if desired, introducing an $R^5$ substituent to produce a compound of the formula

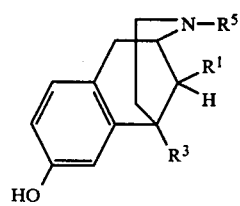

XIV wherein $R^5$ is as defined in formula I other than hydrogen, and $R^1$ and $R^3$ are unchanged; and,
if desired, converting the compound of formula XIV to the compound of formula

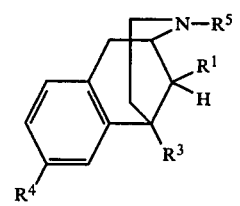

XVI wherein $R^1$, $R^3$ and $R^5$ are as stated above, except that $R^1$ is not hydroxyphenyl or hydroxyheteroaryl, and $R^4$ is alkoxy or acyloxy;

(k) wherein $R^5$ is alkyl, $R^1$, $R^3$ and $R^4$ are as defined in formula I, and $R^2$ is alkoxy, which comprises converting a compound of the formula

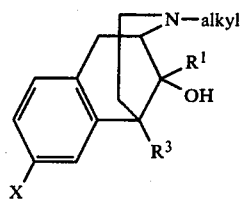

III wherein $R^1$ and $R^3$ are as stated above, except that $R^1$ is not hydroxyphenyl or hydroxyheteroaryl, and X is hydrogen or alkoxy, into an alkali metal hydroxylate and then alkylating the resulting compound to form a compound of the formula

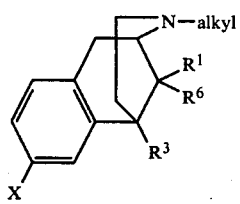

VI wherein $R^1$, $R^3$ and X are unchanged and $R^6$ is alkoxy;
and, if desired, cleaving selectively the aromatic ether function of the compound of formula VI wherein X is alkoxy to produce the corresponding 2'-hydroxy compound of formula

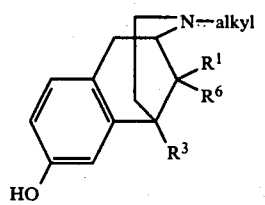

XVIII wherein $R^1$, $R^3$ and $R^6$ are as above stated, except that $R^1$ is not alkoxyphenyl or alkoxyheteroaryl;
and, if desired, converting the compound of formula XVIII into the compound of formula

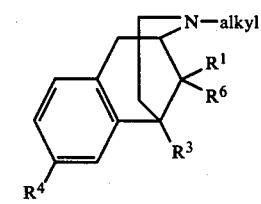

XIX wherein $R^1$, $R^3$ and $R^6$ are as above stated, except that $R^1$ is not hydroxyphenyl or hydroxyheteroaryl, and $R^4$ is alkoxy or acyloxy;

(l) wherein $R^5$ is alkyl, $R^1$, $R^3$ and $R^4$ are as defined in formula I and $R^4$ is not hydrogen, and $R^2$ is alkoxy, which comprises converting a compound of the formula

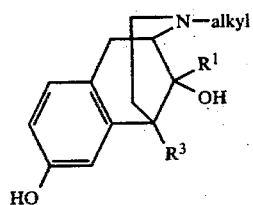 VIII wherein $R^1$ and $R^3$ are as stated above, except that $R^1$ is not alkoxyphenyl or alkoxyheteroaryl, into an alkali metal hydroxylate and then alkylating the resulting compound to form a compound of the formula

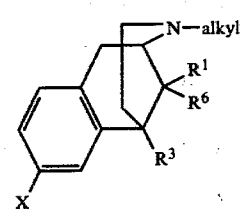 VI wherein X and $R^6$ are each alkoxy and $R^1$ and $R^3$ are as stated above, except that $R^1$ is not hydroxyphenyl or hydroxyheteroaryl;

and, if desired, cleaving selectively the aromatic ether function of the compound of formula VI to produce the corresponding 2'-hydroxy compound of formula

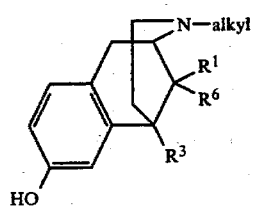 XVIII wherein $R^1$, $R^3$ and $R^6$ are as above stated, except that $R^1$ is not alkoxyphenyl or alkoxyheteroaryl;

and, if desired, converting the compound of formula XVIII into the compound of formula

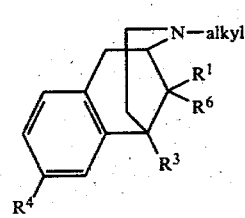 XIX wherein $R^1$, $R^3$ and $R^6$ are as above stated, except that $R^1$ is not hydroxyphenyl or hydroxyheteroaryl, and $R^4$ is alkoxy or acyloxy;

(m) wherein $R^5$ is alkyl, $R^1$ and $R^3$ are as defined in formula I, $R^2$ is acyloxy and $R^4$ is acyloxy, hydroxy or alkoxy, which comprises acylating the compound of formula

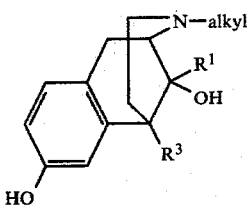 VIII to form the compound of formula

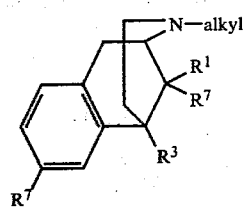 IX wherein $R^7$ (in each case) is acyloxy and $R^1$ and $R^3$ are as stated above;

and, if desired, selectively saponifying the phenolic ester group at the 2'-position to produce a compound of the formula

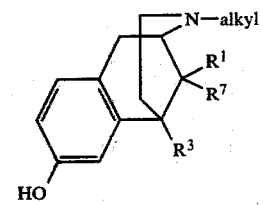 X wherein $R^1$, $R^3$ and $R^7$ are as stated above, except that $R^1$ is not alkoxyphenyl or alkoxyheteroaryl;

and, if desired, alkylating or acylating the 2'-hydroxy group to form a compound of the formula

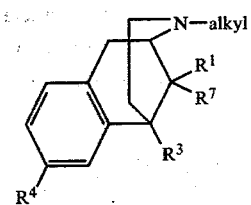 XI wherein $R^4$ is alkoxy or acyloxy, and $R^1$, $R^3$ and $R^7$ are as stated above, except that $R^1$ is not hydroxyphenyl or hydroxyheteroaryl;

(n) wherein $R^5$ is alkyl, $R^1$ and $R^3$ are as defined in formula I, $R^2$ is acyloxy or hydroxy, and $R^4$ is hydrogen or alkoxy when $R^2$ is acyloxy, or $R^4$ is hydroxy when $R^2$ is hydroxy, which comprises acylating a compound of the formula

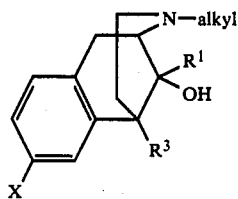

wherein $R^1$ and $R^3$ are as stated above, except that $R^1$ is not hydroxyphenyl or hydroxyheteroaryl, and X is hydrogen or alkoxy, to form a compound of the formula

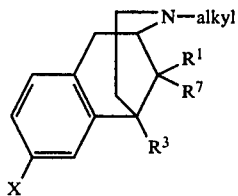

wherein $R^1$, $R^3$ and X are unchanged and $R^7$ is acyloxy; and, if desired, converting the compound of formula VII wherein X is alkoxy, to form the compound of the formula

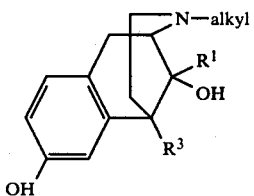

wherein $R^1$ and $R^3$ are as stated above, except that $R^1$ is not alkoxyphenyl or alkoxyheteroaryl;

(o) wherein $R^5$ is alkyl, $R^1$ is as defined in formula I other than hydroxyphenyl or hydroxyheteroaryl, $R^2$ is hydrogen, $R^3$ is as defined in formula I, $R^4$ is hydroxy, and $R^1$ and $R^3$ are cis relative to each other, which comprises subjecting a compound of formula

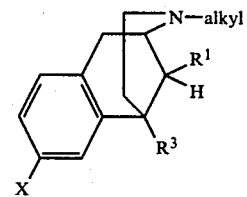

wherein $R^1$ and $R^3$ are as stated above, except that $R^1$ is not hydroxyphenyl or hydroxyheteroaryl, and X is alkoxy, to cleavage of the ether function at the 2'-position to form a compound of formula

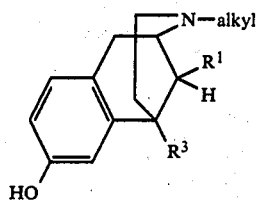

wherein $R^1$ and $R^3$ are as stated above, except that $R^1$ is not alkoxyphenyl or alkoxyheteroaryl;

(p) wherein $R^5$ is alkyl, $R^1$ and $R^3$ are cis relative to each other and are as defined in formula I except that $R^1$ is not alkoxyphenyl or alkoxyheteroaryl and $R^3$ is not alkenyl, $R^2$ is hydrogen and $R^4$ is hydroxy, which comprises reducing a compound of the formula

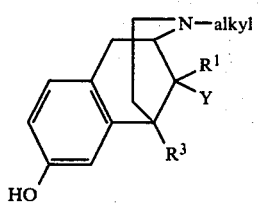

wherein Y is halogen and $R^1$ and $R^3$ are as stated above, to form a compound of the formula

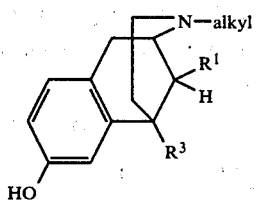

wherein $R^1$ and $R^3$ are as stated above.

In the above processes, when $R^5$ is an alkyl group, it is preferably methyl or ethyl, most preferably methyl. In processes in which compounds of formula XV are produced, $R^1$ is preferably phenyl and $R^3$ is preferably methyl or ethyl, most preferably methyl.

Various reaction sequences for making the compounds of the invention are set out in the accompanying drawing. In the drawing and in the following description, $R^5$ is shown as methyl for simplicity only, it being understood that when $R^5$ is shown as methyl it may alternatively be another alkyl group.

The 9-oxo 6,7-benzomorphans of formula II may be prepared in known manner, for example as described in E. L. May and J. G. Murphy, J. Org. Chem. 20, 257 (1955); J. G. Murphy, J. H. Ager and E. L. May, J. Org. Chem. 25, 1386 (1960); S. Saito and E. L. May, J. Org. Chem. 26, 4536 (1961); Dutch Patent Application No. 73.14758; M. Takeda, H. Inoue, M. Konda, S. Saito and H. Kugita, J. Org. Chem. 37, 2677 (1972); W. J. Ranus, "Improved synthesis and attempted modification of 2'-methoxy-2,5-dimethyl-9-oxo-6,7-benzomorphan", Diss. Univ. Connect. Storrs (Conn.); additional information can be found in the patent specifications and in the communication of J. Monkovic referred to above.

The compounds of formula II may be converted into 9-hydroxy-6,7-benzomorphans of the formula:

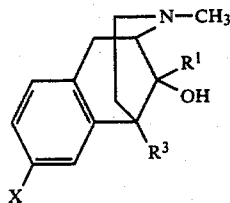
(III)

by reaction with organometallic compounds, preferably organo alkali metal compounds R¹Me, wherein Me is preferably a lithium atom. It is not possible by this reaction to introduce into the benzomorphan nucleus a substituent R¹ which contains an —OH substituent. Thus, in the organo alkali metal compounds R¹Me, R¹ is as defined in formula I but is not hydrogen or a phenyl or heteroaryl group carrying a hydroxy group.

The step of converting compounds of formula II into compounds of formula III using organo alkali metal compounds is believed to be novel in benzomorphan chemistry. Whilst the use of organo-metal compounds is known for introducing small alkyl groups such as methyl or ethyl groups, into 6,7-benzomorphans by reaction with a carbonyl group (at C9) to form tertiary alcohols, it is surprising and highly advantageous that the process can be successfully used to introduce bulky phenyl and heteroaryl groups into the benzomorphan nucleus.

The predominant diastereoisomer of formula III is the one in which the substituents R¹ and R³ are in the cis-position, i.e. the α-isomer. The other isomer, the β-isomer, has the substituents R¹ and R³ in the trans-position. From molecular models of both isomers wherein R¹ is phenyl, it can be seen that in those cases in which R¹ is in the trans-position in relation to R³, ortho hydrogen atoms of the substituent R¹ may approach very closely to the nitrogen atom of the piperidine ring. As a result, in NMR spectra these ortho protons undergo a downfield shift (δ 7.8–8.4 ppm when R¹ is a phenyl group). This deshielding effect is not observed with the isomeric cis compounds. Infrared spectra show that with the α-isomers, as is to be expected, the 9-hydroxy group is hydrogen bonded to the piperidine nitrogen atom, whereas this hydrogen bonding does not occur with the β-isomers. It appears from thin layer chromatography that the β-isomers are less polar than the α-isomers.

The compounds of formula III are compounds of the invention per se, but they can also serve as intermediates for the preparation of other compounds according to the invention. Thus, when treated with a halogenating agent, preferably thionyl chloride, 9-halo-6,7-benzomorphans are obtained with the formula:

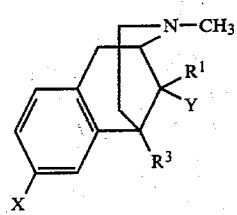
(IV)

wherein Y is a halogen atom in particular chlorine. This halogenation reaction is not useful when the substituent R³ is an alkenyl group, since in that case R³ also enters the reaction.

We believe that, in the compounds of formula IV which are obtained, only one isomer is formed whether the halogenation is carried out on an α- or a β-isomer of compound III. It is believed that, in this isomer, the substituents R¹ and R³ are always cis.

The halogen atom in the compounds of formula IV can be replaced by a hydrogen atom (by reduction) to form compounds of formula:

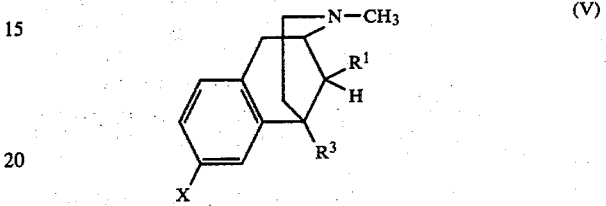
(V)

Suitable reduction methods are, for example, the use of LiAlH₄, cathodic reduction and catalytic hydrogenolysis, the latter generally being the preferred method. However, when another substituent is present which is itself susceptible to catalytic reduction, cathodic reduction is preferred. The use of cathodic reduction in this way in benzomorphan chemistry is believed to be novel. It is a highly advantageous procedure. The compounds of formula V which are formed are mixtures of the two diastereoisomers in which α-isomers predominate.

The compounds of formula V may be obtained directly from the compounds of formula III by a reduction using lithium and liquid ammonia. This reaction is possible whether or not R³ contains an alkenyl group, since the latter is not reduced under these conditions. The α-isomers of compound III should be used as starting materials for this reduction, since a different product is obtained when β-isomers are used. Using only the α-isomer as starting material, the product of formula V is mainly α-isomer although some small amount of β-isomer may be present.

In order to make 6,7-benzomorphans according to formula I in which R² is an alkoxy group, compounds of formula III may be converted into their alkali metal hydroxylates and then alkylated with an alkyl halide, or another suitable alkylating agent, to form compounds of formula:

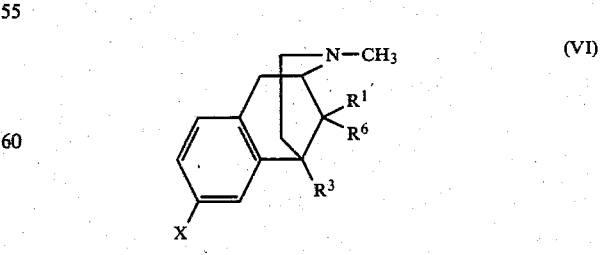
(VI)

wherein R⁶ is an alkoxy group.

Acylation of 6,7-benzomorphans of formula III results in compounds of the formula:

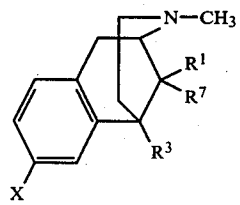

(VII)

wherein R⁷ is an acyloxy group.

The alkoxy, e.g. methoxy, group X in compounds of formula III, V or VI may be converted into a hydroxy group using a suitable ether splitting agent, such as boron tribromide, to give compounds of formula VIII, XV and XVIII, respectively. However, if substituent R³ is an alkenyl group, the use of sodium thioethoxide is more advantageous, cf. G. I. Feutrill and R. W. Mirrington in Tetrahedron Letters 1970, 1327.

It will be appreciated that, when a compound contains two aromatic ether groups, both may be split off in an ether-splitting reaction. This has to be borne in mind when devising a synthesis of a compound of the invention containing, for example, an alkoxy-substituted phenyl group as the R¹ substituent. Ether splitting of such a substituent is, however, a useful way of obtaining a compound of the invention in which R¹ contains a hydroxy substituent (e.g. a hydroxyphenyl or hydroxyheteroaryl).

The compounds of formula VIII

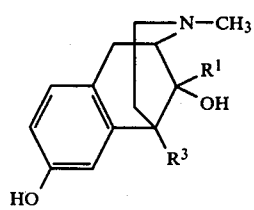

VIII can be made either by ether cleavage of compounds of formula III as hereinbefore described, which is the preferred method, or by splitting of compounds of formulas VI or VII,

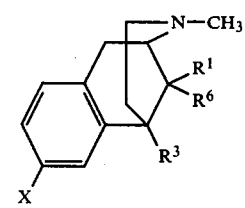

VI

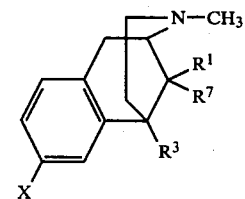

VII wherein X is alkoxy.

Acylation of the compounds of formula VIII gives compounds of formula

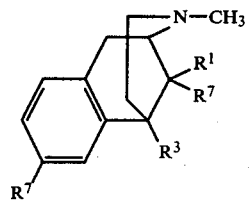

IX wherein R⁷ is an acyloxy group. By selective saponification of the ester group at the 2'-position of the compounds of formula IX, compounds may be obtained of formula:

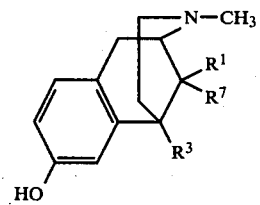

X

The hydroxy group at the 2'-position of these compounds can be alkylated or acylated to form compounds of formula

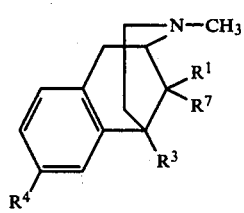

XI wherein R⁴ is an alkoxy or acyloxy group.

It will be appreciated that, when a compound contains two aromatic hydroxy groups, both may be alkylated or acylated. Thus, for example, a hydroxy-substituted phenyl group as the R¹ substituent may be converted to an alkoxy or acyloxy-substituted phenyl group, when 2'-hydroxy-6,7-benzomorphans of the invention are alkylated or acylated.

Compounds of formula VI

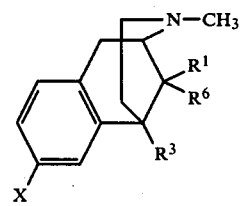

VI wherein R⁶ and X are the same alkoxy groups, can be prepared by alkylation of compounds of the formula

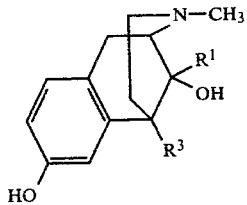

However, in general the preparation of compounds of the formula VI by alkylation of the compounds of formula III, as hereinbefore described, is more preferable.

Compounds of formula XVIII

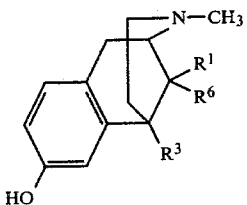

wherein $R^6$ is alkoxy, can be alkylated or acylated to form compounds of the formula

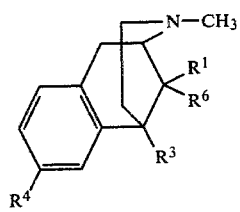

wherein $R^4$ is alkoxy or acyloxy.

Compounds of formula XX

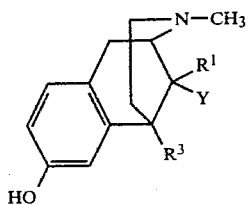

wherein Y is halogen, can be made either by ether cleavage of compounds of formula IV or by halogenation of compounds of formula VIII. Also this halogenation reaction is not useful when the substituent $R^3$ is an alkenyl group, since in that case $R^3$ enters the reaction. The compounds of formula XX can be converted into compounds of formula XV by reduction

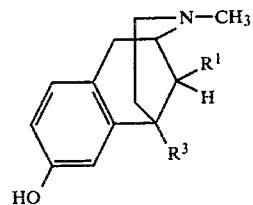

and the compounds of formula XV may be alkylated or acylated to form compounds of formula

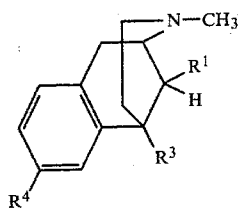

wherein $R^4$ is alkoxy or acyloxy.

The above described syntheses all lead to 6,7-benzomorphans having a methyl group at the 2'-position. However, it will be clear to those skilled in the art, that it is also possible to prepare 6,7-benzomorphans with a different alkyl group at the 2-position by starting from the appropriate N-alkyl starting material.

It has been found that the α-isomers of formula V can be N-demethylated by methods known in benzomorphan chemistry, the preferred method being the von Braun cyanogen bromide procedure. Thus, starting from the α-isomer of formula V, compounds may be obtained of formula:

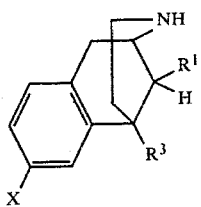

If a mixture of α- and β-isomers is used, only the α-isomer reacts because of steric hindrance in the β-isomer. The substituent $R^5$ can be introduced into these compounds, for example the compounds can be alkylated or acylated (followed by reduction of the resulting amide group), to form compounds of formula

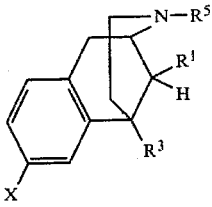

The alkylation and acylation substitution methods are the same as those usually used for the introduction of nitrogen substituents in benzomorphans.

Group X can be converted into $R^4$ as defined in formula I. Thus, compounds of formula XIII may be treated with an ether splitting agent, preferably boron tribromide, when X is alkoxy, to form compounds of the formula:

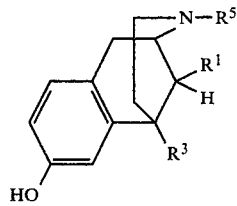
(XIV)

These compounds can be alkylated or acylated, if desired, to form compounds of formula XVI. If the substituent $R^5$ is susceptible to reaction with the ether splitting agent, a reversed order of proceeding is preferred, viz. compounds of formula XII are treated first with the ether splitting agent, giving compounds of formula:

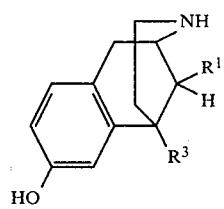
(XIIa)

and then the introduction of $R^5$ is carried out to produce compounds of formula XIV. The latter compounds can be alkylated or acylated, if desired, to give compounds of formula XVI.

The syntheses described above, starting from compounds of formula II wherein X is an alkoxy group, preferably a methoxy group, ultimately result in 6,7-benzomorphans having an oxygen function at position 2'. It will be evident that if, instead, the starting materials are compounds of formula II in which X is a hydrogen atom, the final products of the syntheses will be 6,7-benzomorphans according to the invention, in which the 2'-position is not substituted. These 6,7-benzomorphans may also be obtained by elimination of the 2'-hydroxy group from 6,7-benzomorphans of formula I, wherein $R^4$ is a hydroxy group, by methods for the reductive removal of phenolic hydroxy groups from aromatic nuclei, e.g. reaction with 1-phenyl-5-chlorotetrazole or with dicyclohexyl carbodiimide followed by catalytic reduction of the primary reaction products (cf. W. J. Musliner and J. W. Gates, J.Amer.Chem.Soc. 88, 4271 (1966) and E. Vowinkel and C. Wolff, Chem.Ber. 107, 907 (1974), respectively).

In formulating any particular synthesis for a compound of the invention, those skilled in the art will appreciate that care must be exercised to ensure that only the particular substituent being replaced or modified enters into the reaction concerned. Where two or more substituents are present which could all enter a reaction, then either reactants will be used which are selective or an alternative route may have to be used to obtain the desired compound. It will be clear to those skilled in the art, that in a number of cases, certain reaction steps described may be carried out in a different sequence or simultaneously or without isolating intermediates, and these possibilities are all included in the invention.

As described above, three asymmetric carbon atoms (C1, C5 and C9) are present in the ring system of the compounds of the invention. Because of the fixed character of the bridged tricyclic system (involving C1 and C5) only two racemic pairs of enantiomers can exist. In many of the reactions described, the racemate having $R^1$ and $R^3$ in a cis relation—the α-isomer—always predominates while the trans isomer (β) is in the minority or is not found at all. The isomers can be separated. The α-isomers are the more important ones because of their more pronounced pharmacological activity. The isomers can be resolved into their optically active enantiomers, preferably by separation of their salts with suitable optically active acids. These enantiomers also form part of the invention.

The pharmaceutical compositions of the invention may be formulated in unit dosage forms to be administered orally, parenterally or by suppository. Generally, such dosage forms will contain from 0.1 to 100 mg, preferably 0.1 to 10 mg, of a compound of the invention and may be administered, for example from 1 to 6 times a day.

For oral administration, the compositions may be in the form of pills, solutions, tablets, capsules, or other forms, and may contain the free base or a (pharmaceutically acceptable) salt.

For parenteral administration, for example by injection, the compositions may suitably comprise a solution of a compound of the invention, preferably in the form of a pharmaceutically acceptable salt thereof, in for example water. Generally, the hydrochloride or lactate salts are suitable. The solution will be at a suitable pH and may be made isotonic with glucose or sodium chloride, for example.

In suppositories, the free bases or pharmaceutically acceptable salts may be used, in association with known substances such as cacao-butter.

The compositions of the invention may contain other active compounds, if desired. Combinations of compounds of the invention with dimethyl sulfoxide are also included.

In order that the invention may be more fully understood, the following Examples are given by way of illustration only.

EXAMPLE 1

2,5-Dimethyl-9-hydroxy-2'-methoxy-9-phenyl-6,7-benzomorphan, α-and β- isomers

A solution of 1.5 g of 2,5-dimethyl-2'-methoxy-9-oxo-6,7-benzomorphan hydrochloride in 20 ml of water is shaken with 2 ml of concentrated ammonium hydroxide and 100 ml of ether. The ethereal solution of the free base thus obtained is dried with magnesium sulphate.

To this solution there is added dropwise with stirring under an atmosphere of nitrogen and at room temperature, 20 ml of a 1 molar ethereal solution of phenyl lithium. After two hours the mixture is poured carefully into cold water. After acidification with hydrochloric acid, the aqueous layer is separated, made alkaline with ammonium hydroxide and extracted with chloroform. The dried extract is evaporated in vacuo leaving 1.2 g of a solid mixture of two stereoisomeric bases in a proportion of approximately 3:1. This mixture is dissolved in 20 ml of petroleum ether (boiling range 60°–80° C.) and kept overnight. 500 mg of crystals of the α-isomer separate.

The mother liquor is evaporated in vacuo and the residue submitted to chromatography on a column of 50 g of silica gel with a cyclohexane-acetone (7:3) mixture as the eluant. The less polar β-isomer appaers first in the eluate followed by an additional quantity of the α-isomer.

The yield of the α-isomer is 800 mg, white crystals m.p. 149°–150.5° C. and of the β-isomer 350 mg, white crystals m.p. 115°–117° C.

The α-isomer has a structure in which the 9-phenyl group is in a cis position with respect to the 5-methyl substituent.

NMR (CDCl$_3$): δ (CH$_3$C) 1.42 ppm (s), δ (CH$_3$N) 2.40 ppm (s), δ (CH$_3$O) 3.80 ppm (s), δ (H$_{arom}$) 6.6–7.5 ppm (8H).

In the β-isomer these two substituents are in a trans position to each other.

NMR (CDCl$_3$): δ (CH$_3$C) 1.10 ppm (s), δ (CH$_3$N) 2.40 ppm (s), δ (CH$_3$O) 3.78 ppm (s), δ (H$_{arom}$) 6.6–7.4 ppm (6H), δ (H$_{arom}$) 8.3–8.5 ppm (2H,m).

EXAMPLE 2

5-Ethyl-9-hydroxy-2'-methoxy-2-methyl-9-phenyl-6,7-benzomorphan hydrochloride, α-and β-isomers In a manner similar to the method described in Example 1, but starting from 700 mg of 5-ethyl-2-methyl-2'-methoxy-9-oxo-6,7-benzomorphan and using 15 ml of a 1 molar ethereal phenyl lithium solution, a mixture of two isomeric bases is obtained in 82.5% yield Separation and purification of the isomers is made by column chromatography (silica gel, eluant:benzene-methanol (9:1)). The isomers are isolated as the hydrochlorides, thus obtaining 555 mg of the hydrochloride of the α-isomer (m.p. 237°–241° C. and 244 mg of the hydrochloride of the β-isomer (m.p. 224°–227° C.).

EXAMPLE 3

5-Allyl-9-hydroxy-2'-methoxy-2-methyl-9-phenyl-6,7-benzomorphan, α-and β-isomers In a manner similar to the method described in Example 1, but starting from 2.1 g of 5-allyl-2'-methoxy-2-methyl-9-oxo-6,7-benzomorphan and using 35 ml of a 1 molar ethereal solution of phenyl lithium, a yield of 77% of a mixture of two isomeric bases is obtained. Column chromatography is carried out as described in Example 1, yielding 1.7 g of the α-isomer and 0.3 g of the β-isomer which do not crystallize. The α-isomer is converted to the hydrochloride with m.p. 235°–237° C. (dec). The β-isomer gives a hydrochloride with m.p. 225°–227° C.

EXAMPLE 4

5-(2-Butenyl)-9-hydroxy-2'-methoxy-2-methyl-9-phenyl-6,7-benzomorphan hydrochloride, α-and β-isomers According to the method described in Example 1, but using 5-(2-butenyl)-2'-methoxy-2-methyl-9-oxo-6,7-benzomorphan as the starting material, a mixture of two stereoisomers is obtained. After separation by column chromatography with silica gel as the adsorbent and ethyl acetate as the eluant, the isomers are isolated as the hydrochlorides.

Yield α-isomer 32%, m.p. 231°–233° C. (dec). YIeld β-isomer 13%, m.p. 212°–217° C. (dec).

EXAMPLE 5

2,5-Dimethyl-9-hydroxy-2'-methoxy-9-(p-methoxyphenyl)-6,7-benzomorphan hydrochloride, α-and β-isomers To a rapidly stirred solution of 73.5 mmoles of butyl lithium in a mixture of 45 ml of hexane and 90 ml of dry ether, there is added dropwise, but rather quickly, a solution of 9.12 g (48 mmoles) of p-bromoanisole in 60 ml of dry ether, while keeping the temperature at 15° C. and flushing the mixture with nitrogen. After 10 minutes, a solution of 5.96 g (24.3 mmoles) of 2,5-dimethyl-2'-methoxy-9-oxo-6,7-benzomorphan in 60 ml of dry ether is added dropwise rapidly. After continuous stirring at 20° C. for 2 hours, the reaction mixture is poured into a mixture of ice and water. Processing then follows as described in Example 1. The crude mixture of bases amounts to 9.7 g. It is an oil from which, after column chromatography with silica gel as the adsorbent and toluene—ethyl acetate (8:2) as the eluant, both isomers are obtained. They crystallise as the hydrochlorides. Yield of the α-isomer 4.0 g m.p. 205°–209° C. (dec).

Yield of the β-isomer 0.66 g m.p. 196°–198° C. (dec).

EXAMPLE 6

2,5-Dimethyl-9-hydroxy-2'-methoxy-9-(o-methoxyphenyl)-6,7-benzomorphan hydrochloride, α-isomer In a manner similar to the method described in Example 5, but using o-bromoanisole instead of the para-isomer, a mixture of stereoisomers is obtained which is separated in the usual way by chromatography on silica gel, the eluant being ethyl acetate. The reaction proceeds less smoothly in this case, apparently because of steric hindrance. Besides the isomeric reaction products, some 50% of the starting material can be isolated. The α-isomer of the title compound is obtained as the hydrochloride m.p. 193°–199° C. (dec), yield 20%.

The β-isomer which is not obtained crystalline amounts to 2%.

EXAMPLE 7

2,5-Dimethyl-9-hydroxy-2'-methoxy-9-(p-methylphenyl)-6,7-benzomorphan hydrochloride In a manner similar to the method described in Example 5, but using p-bromotoluene instead of p-bromoanisole, a mixture of isomeric bases is obtained. According to a thin layer chromatogram, the α-and β-isomer are present in a proportion of 4:1. In this case, the column chromatography is omitted and both isomers are obtained as a mixture of the hydrochlorides (yield 70%) to serve as the starting material for conversion into the corresponding 9-chloro compound (Example 19).

EXAMPLE 8

9-(p-Dimethylaminophenyl)-2,5-dimethyl-9-hydroxy-2'-methoxy-6,7-benzomorphan dihydrochloride, α-and β-isomers In a similar manner to that described in Example 5, but using p-bromo-N,N-dimethylaniline instead of p-bromoanisole, a mixture of bases is obtained from which, after chromatographic separation on silica gel with toluene-ethyl acetate (8:2) as the eluant, both isomers are isolated as the dihydrochlorides. Yield of the dihydrochloride of the α-isomer 30%, m.p. 195°–199° C. The β-isomer is obtained in a yield of 15% as an amorphous product.

EXAMPLE 9

2,5-Dimethyl-9-(p-fluorophenyl)-9-hydroxy-2'-methoxy-6,7-benzomorphan hydrochloride In a manner similar to that described in Example 5, but using p-bromofluorobenzene instead of p-bromoanisole, a mixture of isomeric products is obtained which is not separated but converted into a mixture of hydrochlorides (yield 78%) consisting of the α- and β-isomers in a proportion of 4:1.

EXAMPLE 10

2,5-Dimethyl-9-hydroxy-2'-methoxy-9-(m-trifluoromethylphenyl)-6,7-benzomorphan hydrochloride To a cold solution of 1.8 g (8 mmoles) of m-trifluoromethylbromobenzene in 5 ml of dry ether, there is added dropwise over a period of one hour, 3.6 ml of a 15% ethereal solution of butyl lithium (8 mmoles). During the addition, the mixture is stirred continuously and flushed with nitrogen while the temperature is kept at 0°.

After stirring the reaction mixture for an additional 2½ hours at room temperature, a solution of 0.87 g (3.56 mmoles) of 2,5-dimethyl-2'-methoxy-9-oxo-6,7-benzomorphan in 10 ml of dry ether is added dropwise. Another reaction period of 16 hours follows, after which the mixture is poured onto ice. Processing then follows the procedure given in Example 1. The basic fraction (1.3 g) contains the α-and β-isomers in a proportion of 4:1. Separation is effected by chromatography on a silica gel column with ethyl acetate as the eluant. The α-isomer is obtained as the hydrochloride. Yield 540 mg (40%), m.p. 205°-208° C. (recrystallized from methanol-ethyl acetate). The β-isomer is not obtained crystalline.

EXAMPLE 11

2,5-Dimethyl-9-hydroxy-2'-methoxy-9-(2-thienyl)-6,7-benzomorphan hydrochloride, α-and β-isomers A solution of 2-thienyl lithium is made from 1.02 g of thiophene (12 mmoles) dissolved in 50 ml of dry ether and 7.2 ml of a 15% solution of butyl lithium (12 mmoles) in hexane. At room temperature and with mechanical stirring under an atmosphere of nitrogen, there is dropwise added to this solution 870 mg (3.56 mmoles) of 2,5-dimethyl-2'-methoxy-9-oxo-6,7-benzomorphan dissolved in 5 ml of ether. After the elapse of 2 hours, the reaction mixture is poured into water. Working up proceeds as described in the foregoing Examples. Chromatography is carried out on a column of silica gel and with toluene-ethyl acetate (9:1) as the eluant. Both isomers are obtained as the hydrochlorides.

After recrystallization from methanol-ethyl acetate, the α-isomer melts at 236°-239° C. (dec), yield 600 mg (46%) whereas the β-isomer has a m.p. 196°-200° C. (dec), yield 100 mg (8%).

EXAMPLE 12

2,5-Dimethyl-9-hydroxy-2'-methoxy-9-(3-pyridyl)-6,7-benzomorphan dihydrochloride, α-and β-isomers A mixture obtained from 13.8 ml of a 15% solution of butyl lithium (22.5 mmoles) in hexane and 45 ml of dry ether, is stirred at −35° C. under a nitrogen atmosphere while a solution of 3.3 g (21 mmoles) of 3-bromopyridine in 15 ml of dry ether is added dropwise over a period of 10 minutes. Then, still at −35° C., 2.6 g (10.5 mmoles) of 2,5-dimethyl-2'-methoxy-9-oxo-6,7-benzomorphan, dissolved in 24 of dry ether, is added dropwise.

The temperature is allowed to rise to 20° and stirring is continued for 2 hours. The reaction mixture is then poured into water and ice whereafter working up proceeds as described in the foregoing Examples. The oily mixture of bases weighs 5.0 g. The adsorbent in the chromatography is silica gel (150 g) and the eluant ethyl acetate. The α-isomer is isolated as the dihydrochloride, yield 1.96 g (45%) m.p. 255°-258° C. The β-isomer is obtained as a crystalline base, yield 0.84 g (21%) m.p. 147°-150° C.

EXAMPLE 13

2,5-Dimethyl-9-hydroxy-2'-methoxy-9-(4-pyridyl)-6,7-benzomorphan dihydrochloride, α-isomer In a manner identical to that described in Example 12, but using 4-bromopyridine instead of 3-bromopyridine, the title compound is obtained as the crystalline dihydrochloride of the α-isomer which is recrystallized from methanol-ethyl acetate. Yield 40% m.p. 237°-244° C. (dec). A pure β-isomer is not obtained.

EXAMPLE 14

9-Hydroxy-2'-methoxy-2-methyl-9-phenyl-5-propyl-6,7-benzomorphan hydrochloride

A crude mixture of 349 mg of the hydrochlorides of the α-and β-isomers of 5-allyl-9-hydroxy-2'-methoxy-2-methyl-9-phenyl-6,7-benzomorphan, obtained as described in Example 3, is dissolved in 5 ml of absolute ethanol and submitted to catalytic hydrogenation at room temperature and ordinary pressure, the catalyst being 50 mg of 5% Pd on charcoal. The calculated amount of hydrogen is absorbed within 1.5 hours. The catalyst is removed by filtration and the solvent evaporated, leaving 340 mg of a non-crystalline product consisting of a mixture of hydrochlorides of α-and β-isomers. This product is used in the preparation of the corresponding 9-chloro compound as described in Example 17.

EXAMPLE 15

9-Chloro-2,5-dimethyl-2'-methoxy-9-phenyl-6,7-benzomorphan

A mixture of 5 ml of thionyl chloride and 360 mg (1 mmole) of the α-isomer of 2,5-dimethyl-9-hydroxy-2'-methoxy-9-phenyl-6,7-benzomorphan hydrochloride (cf. Example 1) is stirred and heated at 60°-70° C. for 3 hours.

After cooling, the mixture is poured on ice and water. After the addition of ammonium hydroxide to alkalinity, the product separates. It is collected by extraction with chloroform.

The extract is dried and evaporated, leaving 320 mg of the reaction product which crystallizes after the addition of 10 ml of petroleum ether (boiling range 60°-80° C.). White crystals m.p. 127°-131° C. Yield 250 mg.

EXAMPLE 16

9-Chloro-5-ethyl-2'-methoxy-2-methyl-9-phenyl-6,7-benzomorphan hydrochloride

A mixture of the hydrochlorides of the α-and β-isomers (1.120 g) of 5-ethyl-9-hydroxy-2'-methoxy-2-methyl-9-phenyl-6,7-benzomorphan (cf. Example 2) and 7 ml of thionyl chloride is heated at 60°-70° C. for 3 hours.

Processing as described in Example 15 furnishes the title compound (0.9 g; yield 86%) which is converted into the hydrochloride m.p. 222°-225° C. (dec).

EXAMPLE 17

9-Chloro-2'-methoxy-2-methyl-9-phenyl-5-propyl-6,7-benzomorphan hydrochloride

In a manner similar to that described in Example 15, but using 388 mg of a crude mixture of the α-and β-isomers of 9-hydroxy-2'-methoxy-2-methyl-9-phenyl-5-propyl-6,7-benzomorphan hydrochloride (cf. Example 14) as the starting material, 300 mg of the title compound is obtained. Yield 81%. It is converted into the hydrochloride with m.p. 217° C. (dec).

EXAMPLE 18

9-Chloro-2,5-dimethyl-2'-methoxy-9-(p-methoxyphenyl)-6,7-benzomorphan hydrochloride A mixture of 0.9 ml of thionyl chloride and 300 mg of the β-isomer of 2,5-dimethyl-9-hydroxy-2'-methoxy-9-(p-methoxyphenyl)-6,7-benzomorphan hydrochloride (cf. Example 5) is stirred for 48 hours at 20° C. Processing is carried out as described in Example 15 to produce the title compound in a yield of 35%. The hydrochloride melts at 204°–207° C. (dec).

EXAMPLE 19

9-Chloro-2,5-dimethyl-2'-methoxy-9-(p-methylphenyl)-6,7-benzomorphan hydrochloride In a manner similar to that described in Example 15, but using a mixture of the hydrochlorides of the α-and β-isomers of 2,5-dimethyl-9-hydroxy-2'-methoxy-9-(p-methylphenyl)-6,7-benzomorphan (cf. Example 7) as the starting material, the desired product is obtained as the hydrochloride m.p. 227°–232° C., yield 30%.

EXAMPLE 20

9-Chloro-2,5-dimethyl-9-(p-fluorophenyl)-2'-methoxy-6,7-benzomorphan hydrochloride In a manner similar to that described in Example 15, but using a mixture of the hydrochlorides of the α-and β-isomers of 2,5-dimethyl-9-(p-fluorophenyl)-9-hydroxy-2'-methoxy-6,7-benzomorphan (cf. Example 9) as the starting material, the desired title compound is obtained as the hydrochloride m.p. 207°–209° C. (dec). Recrystallization from ethanol-ethyl acetate. Yield 35%.

EXAMPLE 21

2,5-Dimethyl-2'-methoxy-9-phenyl-6,7-benzomorphan hydrochloride, α-and β-isomers A solution of 378 mg of the hydrochloride of 9-chloro-2,5-dimethyl-2'-methoxy-9-phenyl-6,7-benzomorphan (cf. Example 15) in 10 ml of absolute ethanol, is submitted to catalytic hydrogenolysis by shaking the mixture in an atmosphere of hydrogen at ordinary pressure and room temperature the catalyst being 200 mg of 5% Pd on charcoal. The calculated amount of hydrogen is absorbed after 30 minutes. The catalyst is removed by filtration and the filtrate concentrated in vacuo, leaving 370 mg of the crude reaction product. This is a mixture of the α-and β-isomers which is separated by chromatography on a column of 20 g of silica gel. The eluant is a mixture of benzene and methanol in a proportion of 9:1. In this way, after the addition of ethanolic hydrogen chloride, 340 mg of the hydrochloride of the α-isomer (m.p. 241°–244° C. with softening at 230° C.) and 25 mg of the hydrochloride of the β-isomer (m.p. 213°–216° C. with softening at 185° C.) are obtained.

EXAMPLE 22

5-Ethyl-2'-methoxy-2-methyl-9-phenyl-6,7-benzomorphan hydrochloride, α-and β-isomers With 1.96 g (5 mmoles) of 9-chloro-5-ethyl-2'-methoxy-2-methyl-9-phenyl-6,7-benzomorphan hydrochloride (cf. Example 16) as the starting material, a catalytic hydrogenolysis is carried out in the same way as described in Example 21. The reaction product obtained (1.5 g of a mixture of the hydrochlorides of both isomers) is converted into the free bases and submitted to chromatography on a column of 140 g of silica gel with a mixture of benzene and methanol (8:2) as the eluant. After separation, the isomers are isolated as the hydrochlorides, the yield of the α-isomer being 1.0 g, m.p. 236°–246° C., and of the β-isomer 250 mg.

EXAMPLE 23

2'-Methoxy-2-methyl-9-phenyl-5-propyl-6,7-benzomorphan hydrochloride, α-and β-isomers In a manner similar to that described in Example 21, but using 9-chloro-2'-methoxy-2-methyl-9-phenyl-5-propyl-6,7-benzomorphan hydrochloride (cf. Example 17) as the starting material, the title compounds are obtained in yields of 50% for the α-isomer m.p. 202°–206° C., and of 18% for the β-isomer m.p. 205°–210° C.

EXAMPLE 24

2,5-Dimethyl-9-(p-fluorophenyl)-2'-methoxy-6,7-benzomorphan hydrochloride, α-and β-isomers In a manner similar to that described in Example 21, but using 9-chloro-2,5-dimethyl-9-(p-fluorophenyl)-2'-methoxy-6,7-benzomorphan hydrochloride (cf. Example 20) as the starting material, a mixture of both isomers is obtained. The chromatographic separation is carried out with silica gel as the adsorbent and methanol-ethyl acetate (3:1) as the eluant. The α-isomer melts at 222°–232° C. (dec), yield 37.5% and the β-isomer at 213°–218° C. (dec), yield 7%.

EXAMPLE 25

2,5-Dimethyl-2'-methoxy-9-(p-methylphenyl)-6,7-benzomorphan hydrochloride, α-isomer This compound is prepared by cathodic reduction of 9-chloro-2,5-dimethyl-2'-methoxy-9-(p-methylphenyl)-6,7-benzomorphan hydrochloride (cf. Example 19). For that purpose, a solution of 4 g of said 9-chloro compound in 100 ml of methanol containing 4.0 g of tetramethylammonium chloride, is submitted to electrolysis whereby mercury (with a surface of ±25 cm$^2$) serves as the cathode. The anode compartment, consisting of a porous cup (diameter 2 cm) contains water and holds a graphite rod (effective surface 3 cm$^2$) as the anode. The reduction, which takes about one hour, is carried out at initially 20 V while keeping the current constant at 0.5 A. After the solvent has been evaporated, the residue of salts is taken up in water. This aqueous solution is made alkaline by the addition of ammonium hydroxide and then extracted with chloroform. The extract is concentrated in vacuo leaving 3.4 g of a mixture of bases consisting of the α-and β-isomers in a proportion of 20:1. This can be concluded from the NMR spectrum. After chromatography on a column of 180 g of silica gel with

EXAMPLE 26

5-Allyl-2'-methoxy-2-methyl-9-phenyl-6,7-benzomorphan hydrochloride, α-isomer

A 33% dispersion (1.5 g) of lithium metal in petroleum jelly(Vaseline-trade mark), corresponding to 70 mmoles of lithium, is diluted with 25 ml of dry ether. To this suspension there is added dropwise, at room temperature, a solution of 1.4 g (4 mmoles) of the α-isomer of 5-allyl-9-hydroxy-2'-methoxy-2-methyl-9-phenyl-6,7-benzomorphan (cf. Example 3). The stirred and nitrogen flushed mixture is cooled to −40° C. whereafter 75 ml of liquid ammonia is carefully added dropwise. After 15 minutes, a solution of 15 g of bromobenzene in 20 ml of dry ether is added. The blue colour of the reaction mixture disappears. When the ammonia has been evaporated, 25 ml of water and 25 ml of ether are added. The ethereal solution is extracted with dilute hydrochlorice acid. The aqueous extract is made alkaline with ammonium hydroxide and shaken three times with 25 ml of chloroform. The chloroform solution is dried on magnesium sulphate and evaporated under reduced pressure. It leaves 1.1 g of basic material consisting, according to the NMR spectrum, of the title compound blended with a small amount of the corresponding 5-propyl compound. Apparently, the allyl group is not quite inert to these reduction conditions. The hydrochloride melts at 220°–223° C. (dec). No β-isomer is present.

EXAMPLE 27

2,5-Dimethyl-2'-hydroxy-9-phenyl-6,7-benzomorphan hydrobromide and hydrochloride, α-and β-isomers The α-isomer (150 mg) of 2,5-dimethyl-2'-methoxy-9-phenyl-6,7-benzomorphan hydrochloride (cf. Example 21) is refluxed with 5 ml of 47% hydrobromic acid for 3 hours. After cooling, 90 mg of crystals of the hydrobromide of the desired product separate, m.p. 252°–255° C. The crystals are dissolved in water and the aqueous solution is made alkaline with ammonium hydroxide. The base is extracted with chloroform and this extract is processed to furnish the hydrochloride of the α-isomer of the title compound m.p. 243°–246° C. (dec). The β-isomer is obtained in exactly the same way, but starting from the β-isomer of the 2'-methoxy compound (153 mg). The hydrobromide (120 mg) obtained is converted into the hydrochloride m.p. 230° C. (dec).

EXAMPLE 28

5-Ethyl-2'-hydroxy-2-methyl-9-phenyl-6,7-benzomorphan hydrobromide and hydrochloride, α-and β-isomers In a similar manner to that described in Example 27, but starting from the α-isomer (1.2 g) of 5-ethyl-2'-methoxy-2-methyl-9-phenyl-6,7-benzomorphan hydrochloride (cf. Example 22), the α-isomer of the title compound is obtained as the hydrobromide (800 mg or 56%), which is converted into the hydrochloride m.p. 193°–194° C. with softening at 183° with loss of water of crystallization.

EXAMPLE 29

2'-Hydroxy-2-methyl-9-phenyl-5-propyl-6,7-benzomorphan hydrochloride, α-isomer

To a stirred solution of 187 mg (0.5 mmole) of the hydrochloride of 2'-methoxy-2-methyl-9-phenyl-5-propyl-6,7-benzomorphan (cf. Example 23) in 20 ml of dry methylene chloride, there is added dropwise and at −10° C., a solution of 0.10 ml (1 mmole) of boron tribromide in 10 ml of methylene chloride.

The temperature is allowed to rise to 20° C. and the mixture is kept at that temperature for 3 hours. After 20 ml of ether has been added dropwise to decompose halogen boron compounds, the mixture is stirred for 15 minutes and then evaporated in vacuo. The residue is shaken with diluted ammonium hydroxide and chloroform. The chloroform extract is dried and then evaporated, leaving the α-isomer of the title compound in a yield of 70% It is converted into the hydrochloride which melts at 202°–206° C.

EXAMPLE 30

5-Allyl-2'-hydroxy-2-methyl-9-phenyl-6,7-benzomorphan hydrochloride, α-isomer

In a manner similar to that described in Example 29, but starting from 185 mg of the α-isomer of 5-allyl-2'-methoxy-2-methyl-9-phenyl-6,7-benzomorphan hydrochloride (cf. Example 26), the desired title compound is obtained. Yield 150 mg (94%) crude product which is converted into the hydrochloride m.p. 190°–192° C. (dec).

EXAMPLE 31

2,5-Dimethyl-2'-hydroxy-9-(p-methylphenyl)-6,7-benzomorphan oxalate, α-isomer

In a manner similar to that described in Example 27, but using the α-isomer of 2,5-dimethyl-2'-methoxy-9-(p-methylphenyl)-6,7-benzomorphan hydrochloride (cf. Example 25) as the starting material, the title compound is obtained. It is purified by column chromatography with silica gel as the adsorbent and ethyl acetate as the eluant. The compound is isolated as the oxalate which, after recrystallization from acetone, melts at 196°–200° C. (dec).

Yield 30%.

EXAMPLE 32

2,5-Dimethyl-9-(p-fluorophenyl)-2'-hydroxy-6,7-benzomorphan hydrochloride, α-isomer In a manner similar to that described in Example 29, but using the α-isomer of 2,5-dimethyl-9-(p-fluorophenyl)-2'-methoxy-6,7-benzomorphan hydrochloride (cf. Example 24) as the starting material, the title compound is obtained. Yield 54%, m.p. 218°–221° C. (after recrystallization from methanol-ethyl acetate).

EXAMPLE 33

2',9-Dimethoxy-2,5-dimethyl-9-phenyl-6,7-benzomorphan hydrochloride, α-isomer

To a stirred solution of 3.0 g (9.2 mmoles) of the α-isomer of 2,5-dimethyl-9-hydroxy-2'-methoxy-9-phenyl-6,7-benzomorphan (cf. Example 1) in 30 ml of dry tetrahydrofuran, there is added, at 0° C., 6 ml (120 mmoles) of methyl iodide and 3 g (125 mmoles) of sodium hydride as a 50% suspension in oil, whereafter stirring is continued for 3 hours at room temperature and in an atmosphere of nitrogen. Then the mixture is poured into water. The precipitate is filtered off, washed with water and dried in vacuo. It consists of the methiodide of the title compound. Yield 1.7 g (43%) m.p. 230° C. A mixture of this methiodide and 2.0 g (7.5 mmoles) of triphenylphosphine and 15 ml of dimethylformamide is refluxed for 3 hours. After cooling, the mixture is poured into water. The aqueous mixture is acidified by the addition of hydrochloric acid and then shaken with toluene in order to remove the triphenylphosphine.

Next it is made alkaline using ammonium hydroxide and is extracted again with toluene. The toluene extract is washed with water, dried and evaporated, leaving the title compound as a syrupy base (1.3 g). It is converted into the hydrochloride by the addition of hydrogen chloride in isopropanol. After crystallization from methanol-ethyl acetate, the yield is 1.3 g (85%) of white crystals m.p. 239°–241° C.

EXAMPLE 34

2',9-Dimethoxy-2,5-dimethyl-9-phenyl-6,7-benzomorphan hydrochloride, β-isomer

To a stirred and nitrogen-flushed solution of 1.4 g (4.35 mmoles) of the β-isomer of 2,5-dimethyl-9-hydroxy-2'-methoxy-9-phenyl-6,7-benzomorphan (cf. Example 1) in 16 ml of tetrahydrofuran, there is added 3.2 ml (65 mmoles) of methyl iodide and then, at 0°, 1.6 g of sodium hydride (32 mmoles). After a reaction period of 3 hours at room temperature, water and ether are added carefully.

Then the mixture is acidified and the organic layer separated. The aqueous solution, after being made alkaline with ammonium hydroxide, is extracted with toluene. Evaporation of the extract gives 1.0 g (70%) of the title compound as a base which melts at 179°–181° C. It is converted into the hydrochloride (1.07 g) m.p. 177°–180° C.

EXAMPLE 35

2,5-Dimethyl-9-ethoxy-2'-methoxy-9-phenyl-6,7-benzomorphan hydrochloride, α-isomer In a manner similar to that described in Example 34, but starting from the α-isomer of 2,5-dimethyl-9-hydroxy-2'-methoxy-9-phenyl-6,7-benzomorphan (cf. Example 1) and using ethyl iodide as the alkylating agent at reflux temperature, the title compound is obtained. It is isolated as the hydrochloride which recrystallizes from methanol-ethyl acetate. Yield 40%, m.p. 240°–244° C.

EXAMPLE 36

2,5-Dimethyl-9-ethoxy-2'-methoxy-9-phenyl-6,7-benzomorphan hydrochloride, β-isomer In a manner similar to that described in Example 35, but using the β-isomer instead of the α-isomer of the starting material (cf. Example 1), the title compound is obtained as the hydrochloride. After recrystallization from methanol-ethyl acetate it melts at 182°–184° C. Yield 75%.

EXAMPLE 37

2,5-Dimethyl-2'-methoxy-9-phenyl-9-propoxy-6,7-benzomorphan oxalate, α-isomer

In a manner similar to that described in Example 35, but using n-propyl bromide as the alkylating agent and refluxing for 48 hours, the title compound is obtained as the oxalate, which is recrystallized from acetone. Yield 58%, m.p. 227°–230° C.

EXAMPLE 38

5-Allyl-2',9-dimethoxy-2-methyl-9-phenyl-6,7-benzomorphan hydrochloride, α-isomer A mixture of 1.4 g (4.0 mmoles) of the α-isomer of 5 allyl-9-hydroxy-2'-methoxy-2-methyl-9-phenyl-6,7-benzomorphan (cf. Example 3), 25 ml of tetrahydrofuran and 5.68 g of methyl iodide (40 mmoles) is stirred at 0° C. while 0.9 g (20 mmoles) of sodium hydride is added. Stirring is continued at 40° C. for 1.5 hours. Then, 20 ml of water is added carefully. The mixture is taken to dryness in vacuo. The residue is extracted with 50 ml of toluene. Evaporation of the toluene leaves 1.14 g (78%) of the base which is converted into the hydrochloride m.p. 174°–177° C. (dec).

EXAMPLE 39

5-Allyl-2',9-dimethoxy-2-methyl-9-phenyl-6,7-benzomorphan hydrochloride, β-isomer In a manner similar to that one described in Example 38, but using the corresponding β-isomer as the starting material, the title compound is obtained in a yield of 80%, m.p. of the hydrochloride 195°–198° C.

EXAMPLE 40

9-Acetoxy-2,5-dimethyl-2'-methoxy-9-phenyl-6,7-benzomorphan oxalate, α-isomer

A mixture of 4.8 g of 100% phosphoric acid, 20 ml of acetic anhydride and 1.8 g (5.6 mmoles) of the α-isomer of 2,5-dimethyl-9-hydroxy-2'-methoxy-9-phenyl-6,7-benzomorphan (cf. Example 1) is stirred and heated at 60° for 30 minutes. After cooling, water is added carefully, followed by ammonium hydroxide to make the mixture alkaline. It is then extracted with ether. From this extract, after evaporation, 1.6 g of the free base of the desired product is obtained as a syrup, which is dissolved in acetone. From this solution, the oxalate precipitates by the addition of oxalic acid dissolved in acetone. Yield 1.7 g (65%) m.p. 210°–212° C.

EXAMPLE 41 b

2',9-Dihydroxy-2,5-dimethyl-9-phenyl-6,7-benzomorphan, α-isomer

To a stirred solution of 400 mg (1.11 mmoles) of the α-isomer of 2,5-dimethyl-9-hydroxy-2'-methoxy-9-phenyl-6,7-benzomorphan hydrochloride (cf. Example 1) in 10 ml of dry methylene chloride there is added, dropwise at room temperature and within a period of 10 minutes, a solution of 0.5 ml of boron tribromide in 10 ml of methylene chloride. Stirring is continued for 3 hours. The mixture is poured on ice and water. The aqueous layer is extracted with ether and then made alkaline with ammonium hydroxide. The desired product separated as a crystalline precipitate. Yield 330 mg (97%) m.p. 185°–188° C.

EXAMPLE 42

2',9-Dihydroxy-2,5-dimethyl-9-phenyl-6,7-benzomorphan hydrochloride, β-isomer

By reaction of 280 mg (0.78 mmoles) of the hydrochloride of the β-isomer of the starting material of Example 41 with boron tribromide in a manner similar to that described in Example 41, the title compound is prepared. In this case, however, the basification with ammonium hydroxide does not cause the separation of a crystalline product. Therefore, the aqueous mixture is extracted with chloroform. From this extract, after being dried and evaporated, the desired compound is obtained as a non-crystalline base. Yield 218 mg, 90%. The hydrochloride melts at 175°–185° C. with softening at 156° C.

EXAMPLE 43

5-Allyl-2′,9-dihydroxy-2-methyl-9-phenyl-6,7-benzomorphan hydrochloride, α-isomer This compound is obtained by the reaction of the hydrochloride of the α-isomer of 5-allyl-9-hydroxy-2′-methoxy-2-methyl-9-phenyl-6,7-benzomorphan (cf. Example 3) with boron tribromide in a manner similar to that described in Example 29. From 1.4 g (3.62 mmoles) of starting material, 900 mg (74%) of the product is obtained as as base which is converted into the hydrochloride m.p. 252°–254° C.

EXAMPLE 44

2,5-Dimethyl-2′-hydroxy-9-methoxy-9-phenyl-6,7-benzomorphan oxalate, α-isomer

To a stirred solution of 1.3 g (3.5 mmoles) of the hydrochloride of the α-isomer of 2′,9-dimethoxy-2,5-dimethyl-9-phenyl-6,7-benzomorphan (cf. Example 33) in 48 ml of dry methylene chloride, there is added dropwise 0.72 ml (7.2 mmoles) of boron tribromide dissolved in 10 ml of methylene chloride.

Stirring is continued at room temperature for 1 hour. Then the excess of boron tribromide is decomposed by the addition of ether. This causes the formation of a precipitate which is filtered off, washed with ether and then treated with concentrated ammonium hydroxide.

The basic product so obtained is dissolved in acetone. From this solution a crystalline oxalate is obtained by the addition of oxalic acid dissolved in acetone. It is recrystallized from absolute ethanol. Yield 460 mg (37%), m.p. 230°–232° C.

EXAMPLE 45

2,5-Dimethyl-2′-hydroxy-9-methoxy-9-phenyl-6,7-benzomorphan oxalate, β-isomer

In a manner simular to that described in Example 44, but starting from the corresponding β-isomer, the title compound is obtained as the oxalate. Yield 60%, recrystallized from methanol-ethyl acetate, m.p. 202°–204° C.

EXAMPLE 46

2,5-Dimethyl-9-ethoxy-2′-hydroxy-9-phenyl-6,7-benzomorphan oxalate, α-isomer

In a manner similar to that described in Example 44, but using the hydrochloride of the α-isomer of 2,5-dimethyl-9-ethoxy-2′-methoxy-9-phenyl-6,7-benzomorphan (cf. Example 35) as the starting material, the above compound is obtained as the oxalate, which is recrystallized from methanol-ethyl acetate. Yield 80%, m.p. 226°–228° C.

EXAMPLE 47

2,5-Dimethyl-9-ethoxy-2′-hydroxy-9-phenyl-6,7-benzomorphan oxalate, β-isomer

In a manner similar to that described in Example 46, but starting from the corresponding β-isomer (cf. Example 36), the title compound is obtained as the oxalate which is purified by recrystallization from methanol-ethyl acetate. Yield 60%, m.p. 195°–197° C.

EXAMPLE 48

2,5-Dimethyl-2′-hydroxy-9-phenyl-9-propoxy-6,7-benzomorphan hydrochloride, α-isomer In a manner similar to that described in Example 44, the hydrochloride of the α-isomer of 2,5-dimethyl-2′-methoxy-9-phenyl-9-propoxy-6,7-benzomorphan (cf. Example 37) is treated with boron tribromide. The product crystallizes as the hydrochloride from methanol-ethyl acetate. Yield 60%, m.p. 255°–257° C.

EXAMPLE 49

5-Allyl-2′-hydroxy-9-methoxy-2-methyl-9-phenyl-6,7-benzomorphan hydrochloride, α-isomer A suspension obtained by mixing 25 ml of dimethyl formamide and 400 mg of a 60% dispersion of sodium hydride in mineral oil (corresponding to 10 mmoles of sodium hydride) is stirred at 0° C. under an atmosphere of nitrogen while a solution of 840 mg (12 mmoles) of ethyl mercaptan is added dropwise within a period of 10 minutes. Stirring is continued at room temperature for 30 minutes, when 200 mg (0.5 mmoles) of the hydrochloride of the α-isomer of 5-allyl-2′,9-dimethoxy-2-methyl-9-phenyl-6,7-benzomorphan (cf. Example 38), suspended in 20 ml of dimethyl formamide, is added. The mixture is refluxed for 3 hours. Then the solvent is evaporated under reduced pressure. The residue is shaken with 25 ml of water, 50 ml of toluene and sufficient 2 N hydrochloric acid to make the mixture acid. The toluene layer is extracted another two times with 20 ml of 2 N hydrochloric acid. The combined aqueous extracts are made alkaline with ammonium hydroxide. The desired product is taken up in chloroform. After drying and evaporation of the chloroform, 150 mg of the title compound is obtained (86%). The hydrochloride is prepared in the usual way, m.p. 262°–265° C. with softening at 257° C.

EXAMPLE 50

9-Acetoxy-2,5-dimethyl-2′-hydroxy-9-phenyl-6,7-benzomorphan oxalate, α-isomer

In a manner similar to that described in Example 40, but using the α-isomer of 2,5-dimethyl-2′,9-dihydroxy-9-phenyl-6,7-benzomorphan (cf. Example 41) as the starting material, 2′,9-diacetoxy-2,5-dimethyl-9-phenyl-6,7-benzomorphan is obtained as the hydrochloride. This compound is dissolved in methanol and a catalytic amount of p-toluene sulphonic acid is added.

This mixture is refluxed for 2 hours whereby the 2′-acetoxy group is split off selectively. The crude product is purified by chromatography on a column of aluminium oxide. The eluant is a mixture of toluene and ethyl acetate (9:1). The substance is obtained as the oxalate (from acetone). Yield 20%, m.p. 182°–185° C.

EXAMPLE 51

2′-Methoxy-5-methyl-9-phenyl-6,7-benzomorphan hydrochloride, α-isomer

A mixture of 17.4 g (56.8 mmoles) of the α-isomer of 2,5 dimethyl-2′-methoxy-9-phenyl-6,7-benzomorphan (cf. Example 21) as the free base, 150 ml of ethanol-free chloroform and 16.4 g (154.8 mmoles) of cyanogen bromide is stirred and refluxed for 20 hours. Then the mixture is concentrated in vacuo. The oily residue is shaken with 250 ml of toluene and dilute hydrochloric acid. The toluene layer is dried with magnesium sulphate. Evaporation of the solvent leaves a crystalline substance, viz 2-cyano-2'-methoxy-5-methyl-9-phenyl-6,7-benzomorphan, m.p. 152°–156° C. (with softening at 147° C.). Yield 89%. A mixture of this product (16.0 g or 50.3 mmoles), 120 ml of acetic acid and 480 ml of 2 N hydrochloric acid is refluxed for 16 hours in an atmosphere of nitrogen. The resulting clear solution is concentrated in vacuo leaving a crystalline residue which is suspended in 250 ml of water. This suspension is made alkaline with ammonium hydroxide and then extracted with chloroform. Evaporation of the chloroform extract leaves a non-crystalline residue which is heated with a solution of hydrogen chloride in isopropyl alcohol. After the solvent has been stripped off in vacuo, the residue is treated with acetone which causes the crystallization of the hydrochloride. Yield 13,5 (17%). It recrystallizes from a mixture of methanol and ethyl acetate; m.p. 118°–125° C.

EXAMPLE 52

2'-Hydroxy-5-methyl-9-phenyl-6,7-benzomorphan hydrochloride, α-isomer.

This product is prepared in a manner similar to that described in Example 29, but using 1.95 g (5.9 mmoles) of the hydrochloride of the α-isomer of 2'-methoxy-5-methyl-9-phenyl-6,7-benzomorphan (cf. Example 51) as the starting material. The product is isolated as the hydrochloride which, after recrystallization from methanol-ethyl acetate, melts at 285°–289° C. (dec). Yield 1.2 g (63%). If, however, the primary reaction mixture is not processed as described in Example 29 but, instead of being evaporated, is diluted with ether then the hydrobromide of the desired product precipitates. This hydrobromide is used as a starting material in some of the following Examples. It melts at 278°–284° C. (dec).

EXAMPLE 53

2-Cyclobutylmethyl-2'-methoxy-5-methyl-9-phenyl-6,7-benzomorphan hydrochloride, α-isomer To a stirred mixture of 1.5 g (4.55 mmoles) of the hydrochloride of the α-isomer of 2'-methoxy-5-methyl-9-phenyl-6,7-benzomorphan hydrochloride (cf. Example 51), 20 ml of dry methylene chloride and 9.2 ml of triethylamine, there is added dropwise a solution of 1.6 g (13.65 mmoles) of cyclobutane-carbonyl chloride. During the addition a precipitate appears. The reaction mixture is stirred and refluxed for 2 hours and then cooled to room temperature. Water (100 ml) is added whereafter the diluted mixture is extracted with chloroform. The dried and evaporated extract leaves an oil which is purified by chromatography on a column of 80 g of silica gel. The eluant is a mixture of cyclohexane and acetone (3:1). The obtained oily N-cyclobutanecarbonyl derivative (1.7 g) is dissolved in 50 ml of dry tetrahydrofuran. This solution is added dropwise to a stirred and nitrogen-flushed suspension of 0.5 g (13.6 mmoles) of lithium aluminium hydride in 12.5 ml of dry tetrahydrofuran. Stirring is continued for an additional 30 minutes when 6 ml of ethyl acetate is added dropwise, the mixture being cooled and stirred intensively. After the addition of 50 ml of an aqueous saturated ammonium chloride solution, the suspension obtained is filtered. The filter cake is washed thoroughly with tetrahydrofuran. The combined filtrates are separated into an organic and an aqueous phase. The latter is extracted with ether. Finally the combined organic solutions (filtrate and extract) are dried and evaporated in vacuo.

A non-crystalline basic product remains. It is converted into the hydrochloride by means of hydrogen chloride dissolved in isopropyl alcohol. Addition of acetone completes the crystallization. White crystals m.p. 235°–239° C. (dec). Yield 67%.

EXAMPLE 54

2'-Methoxy-5-methyl-2-phenethyl-9-phenyl-6,7-benzomorphan hydrochloride, α-isomer In a manner similar to that described in Example 53, but using 2.1 g (13.65 mmoles) of phenacetyl chloride as the acylating agent, 1.9 g of N-phenylacetylated product is obtained which after reduction with lithium aluminium hydride gives 650 mg (33%) of the hydrochloride of the title compound. It crystallizes from a mixture of acetone and petroleum ether (boiling range 60°–80° C.), m.p. 216°–221° C. (dec).

EXAMPLE 55

2-Furfuryl-2'-methoxy-5-methyl-9-phenyl-6,7-benzomorphan hydrochloride, α-isomer In a manner similar to that described in Example 53, but using 1.8 g (13.65 mmoles) of furoyl chloride as the acylating agent, 1.4 g of N-furoylated product is obtained which is converted into the title compound by means of reduction with lithium aluminium hydride, giving the title compound as the crystalline hydrochloride. Yield 1.0 g (54%) m.p. 220°–225° C. (dec) after crystallization from acetone-petroleum ether.

EXAMPLE 56

2'-Methoxy-5-methyl-9-phenyl-2-(tetrahydrofurfuryl)-6,7-benzomorphan hydrochloride, α-isomer A mixture of 1.5 g (4.55 mmoles) of the hydrochloride of the α-isomer of 2'-methoxy-5-methyl-9-phenyl-6,7-benzomorphan (cf. Example 51), 10 ml of dry dimethylformamide, 1.2 g (12 mmoles) of potassium hydrogencarbonate and 0.8 g (5 mmoles) of tetrahydrofurfuryl bromide, is stirred and heated at 100°–110° C. in an atmosphere of nitrogen for 24 hours. After cooling, the mixture is diluted with 100 ml of water and then extracted with toluene. The extract leaves, after evaporation, a residue which is submitted to chromatography on a column of 80 g of silica gel. The eluant is a mixture of cyclohexane and acetone (3:1). The effluent is concentrated and the remaining basic product is converted into the hydrochloride which crystallizes from acetone. Yield 600 mg (33%), m.p. 208°–224° C. (dec).

EXAMPLE 57

2-Cyclobutylmethyl-2'-hydroxy-5-methyl-9-phenyl-6,7-benzomorphan hydrochloride, α-isomer In a manner similar to that described in Example 29, but starting from 1.2 g (3.02 mmoles) of the hydrochloride of the α-isomer of 2-cyclobutylmethyl-2'-methoxy-5-methyl-9-phenyl-6,7-benzomorphan (cf. Example 53), the title product is obtained as the hydrochloride. It crystallizes from methanol-ethyl acetate. Yield 500 mg (43%) m.p. 224°–230° C. (dec).

EXAMPLE 58

2'-Hydroxy-5-methyl-2-phenethyl-9-phenyl-6,7-benzomorphan hydrochloride, α-isomer In a manner similar to that described in Example 29, but using 650 mg (1.50 mmoles) of the hydrochloride of the α-isomer of 2'-methoxy-5-methyl-2-phenethyl-9-phenyl-6,7-benzomorphan (cf. Example 54) as the starting material, the title product is obtained as the hydrochloride. It is recrystallized from methanol-ethyl acetate. Yield 250 mg (39%), m.p. 270°–275° C. (dec) with softening at 265° C.

EXAMPLE 59

2-Furfuryl-2'-hydroxy-5-methyl-9-phenyl-6,7-benzomorphan hydrochloride, α-isomer In a manner similar to that described in Example 29, but starting from 1.0 g (2.44 mmoles) of the hydrochloride of the α-isomer of 2-furfuryl-2'-methoxy-5-methyl-9-phenyl-6,7-benzomorphan (cf. Example 55), the title compound is obtained as the hydrochloride which is recrystallized from methanol-ethyl acetate. Yield 360 mg (37.5%) m.p. 245°–251° C. (dec).

EXAMPLE 60

2'-Hydroxy-5-methyl-9-phenyl-2-tetrahydrofurfuryl-6,7-benzomorphan hydrochloride, α-isomer In a manner similar to that described in Example 56, but using 900 mg (2.5 mmoles) of the hydrobromide of the α-isomer of 2'-hydroxy-5-methyl-9-phenyl-6,7-benzomorphan (cf. Example 52), the title compound is obtained. In this case, the crude product is extracted from the diluted reaction mixture using chloroform instead of toluene. The base is purified by chromatography on a column of 80 g of silica gel with methanol as the eluant. The compound is secured as the hydrochloride which is recrystallized from methanol-ethyl acetate. Yield 180 mg (17%), m.p. 262°–265° C. (with slow decomposition starting at 175° C.). As the tetrahydrofurfuryl group possesses an asymmetric carbon atom, the formation of two diastereoisomers may be expected, which apparently occurs in this case.

EXAMPLE 61

2'-Hydroxy-2-(3-methyl-2-butenyl)-5-methyl-9-phenyl-6,7-benzomorphan hydrochloride, α-isomer A mixture of 1.0 g (2.78 mmoles) of the hydrobromide of the α-isomer of 2'-hydroxy-5-methyl-9-phenyl-6,7-benzomorphan (cf. Example 52), 0.83 g (8.34 mmoles) of potassium hydrogencarbonate, 8 ml of dimethylformamide and 0.46 mg (3.06 mmoles) of 3-methyl-2-butenyl bromide is stirred and heated at 80° C. in an atmosphere of nitrogen for 1.5 hours. The mixture is cooled, diluted with 100 ml of water and then extracted with chloroform. Removal of the solvent by evaporation leaves the product as a base which is purified by chromatography on a column of 80 g of silica gel with a mixture of cyclohexane-acetone (3:1) as the eluant. The base is converted into the hydrochloride. Yield 220 mg (20.5%), m.p. 219°–225° C. (dec).

EXAMPLE 62

2'-Hydroxy-5-methyl-9-phenyl-2-propargyl-6,7-benzomorphan hydrochloride, α-isomer In a manner similar to that described in Example 61, but using 0.9 g (2.5 mmoles) of the same starting material with 0.2 g (2.75 mmoles) of propargyl chloride as the alkylating agent, the title compound is obtained. The hydrochloride is obtained in a yield of 400 mg (45%), m.p. 219°–223° C. (dec).

EXAMPLE 63

2'-Hydroxy-2-(2-methoxyethyl)-5-methyl-9-phenyl-6,7-benzomorphan hydrochloride, α-isomer The hydrobromide (1.2 g or 3.33 mmoles) of the α-isomer of 2'-hydroxy-5-methyl-9-phenyl-6,7-benzomorphan (cf. Example 52) is N-acylated with 1.1 g (10.0 mmoles) of methoxyacetyl chloride in a manner similar to that described in Example 53. The product is purified by chromatography on a column of 80 g of silica gel with cyclohexane-acetone (3:1) as the eluant and subsequently reduced to the title compound by means of lithium aluminium hydride. It is isolated as the hydrochloride. Yield 950 mg (76%). After recrystallization from methanol-ethyl acetate, it melts at 234°–237° C. (dec).

EXAMPLE 64

2',9-Dihydroxy-2,5-dimethyl-9-(3-pyridyl)-6,7-benzomorphan dihydrochloride, α-isomer By the method described in Example 29, but using the dihydrochloride of the α-isomer of 2,5-dimethyl-9-hydroxy-2'-methoxy-9-(3-pyridyl)-6,7-benzomorphan (cf. Example 12), the above compound is obtained. The dihydrochloride melts at 284°–288° C. (dec). Yield 60%.

EXAMPLE 65

2',9-Dihydroxy-2,5-dimethyl-9-(p-hydroxyphenyl)-6,7-benzomorphan hydrochloride, α-isomer By the method described in Example 29, but using the hydrochloride of the α-isomer of 2,5-dimethyl-9-hydroxy-2'-methoxy-9-(p-methoxyphenyl)-6,7-benzomorphan (cf. Example 5) and using twice the quantity of boron tribromide, the above compound is obtained as the hydrochloride. Yield 90%, m.p. 210°–215° C.

EXAMPLE 66

2-Ethyl-2'-hydroxy-5-methyl-9-phenyl-6,7-benzomorphan hydrochloride, α-isomer

In a manner similar to that described in Example 61, but using 1.5 g (4.17 mmoles) of the same starting material with 0.5 g (4.6 mmoles) of ethyl bromide as the alkylating agent, the title compound is obtained. This time the reaction is carried out at 80° C. (20 hours). The hydrochloride is recrystallized from methanol-ethyl acetate. Yield 0.88 g (61%), m.p. 255°–265° C. (dec).

EXAMPLE 67

2-n-Hexyl-2'-hydroxy-5-methyl-9-phenyl-6,7-benzomorphan hydrochloride, α-isomer

In a manner similar to that described in Example 61, but using 1.5 g (4.17 mmoles) of the same starting material with 0.76 (4.6 mmoles) of n-hexyl bromide as the alkylating agent, the title compound is obtained. This time the reaction is carried out at 70° C. (20 hours). The hydrochloride is recrystallized from methanol-ethyl acetate. Yield 0.8 g (48%), m.p. 196°–205° C. (dec).

EXAMPLE 68

2-n-Butyl-2'-hydroxy-5-methyl-9-phenyl-6,7-benzomorphan hydrochloride, α-isomer

In a manner similar to that described in Example 61, but using 1.5 g (4.17 mmoles) of the same starting material with 0.63 g (4.6 mmoles) of n-butyl bromide as the alkylating agent, the title compound is obtained. This time the reaction is carried out at 80° C. (4 hours). The hydrochloride is recrystallized from methanol-ethyl acetate. Yield 1.03 g (65%), m.p. 203°–210° C. (dec).

EXAMPLE 69

2-Allyl-2'-hydroxy-5-methyl-9-phenyl-6,7-benzomorphan hydrochloride, α-isomer

In a manner similar to that described in Example 61, but using 3.0 g (8.3 mmoles) of the same starting material with 1.1 g (9.2 mmoles) of allyl bromide as the alkylating agent, the title compound is obtained. This time the reaction is carried out at 80° C. (4 hours). The hydrochloride is recrystallized from methanol-ethyl acetate. Yield 1.54 g (52%), m.p. 242°–250° C. (dec).

EXAMPLE 70

2'-Hydroxy-5-methyl-9-phenyl-2-propyl-6,7-benzomorphan hydrochloride, α-isomer

2-Allyl-2'-hydroxy-5-methyl-9-phenyl-6,7-benzomorphan hydrochloride, α-isomer, 1.2 g (3.4 mmoles) obtained as described in Example 69, is dissolved in 50 ml of absolute ethanol and submitted to catalytic hydrogenation at room temperature and ordinary pressure, the catalyst being 380 mg of 5% palladium on charcoal. The calculated amount of hydrogen is absorbed within 2.5 hours. The catalyst is removed by filtration and the solvent evaporated, leaving 1.2 g of the title compound. The residue is crystallized from methanol-ethyl acetate. Yield 770 mg (65%), m.p. 255°–262° C. (dec).

EXAMPLE 71

2-Cyclopropylmethyl-2'-hydroxy-5-methyl-9-phenyl-6,7-benzomorphan hydrochloride, α-isomer The hydrobromide (2.5 g or 6.9 mmoles) of the α-isomer of 2'-hydroxy-5-methyl-9-phenyl-6,7-benzomorphan (cf. Example 52) is N-acylated with 2.19 g (21 mmoles) of cyclopropanecarbonyl chloride in a manner similar to that described in Example 53. The product is purified by chromatography on a column of 180 g of silica gel with cyclohexane-acetone (3:1) as the eluant and subsequently reduced to the title compound using lithium aluminium hydride as the reducing agent. The compound is isolated as the hydrochloride. Yield 1.1 g (40%). After recrystallization from methanol-ethyl acetate it melts at 260°–265° C. (dec).

EXAMPLE 72

2-(1-Cyclohexenylmethyl)-2'-hydroxy-5-methyl-9-phenyl-6,7-benzomorphan hydrochloride, α-isomer In a manner similar to that described in Example 61, but using 1.0 g (2.78 mmoles) of the same starting material with 0.4 g (3 mmoles) of 1-chloromethylcyclohexane as the alkylating agent, the title compound is obtained. This time the reaction is carried out at 90° C. (4 hours). The hydrochloride is recrystallized from methanol-ethyl acetate. Yield 300 mg (26%), m.p. 249°–251° C.

EXAMPLE 73

2-Cyclopentyl-2'-hydroxy-5-methyl-9-phenyl-6,7-benzomorphan hydrochloride, α-isomer In a manner similar to that described in Example 61, but using 1.0 g (2.78 mmoles) of the same starting material with 0.5 g (3.3 mmoles) of cyclopentyl bromide as the alkylating agent, the title compound is obtained. This time the reaction is carried out at 90° C. (20 hours). The hydrochloride is recrystallized from methanol-ethyl acetate. Yield 320 mg (30%), m.p. 257°–260° C. (dec).

EXAMPLE 74

2'-Hydroxy-2-{2-(p-methoxyphenyl)ethyl}-5-methyl-9-phenyl-6,7-benzomorphan hydrochloride, α-isomer The hydrobromide (1.5 g or 4.17 mmoles) of the α-isomer of 2'-hydroxy-5-methyl-9-phenyl-6,7-benzomorphan (cf. Example 52) is N-acylated with 2.3 g (12.5 mmoles) of p-methoxyphenylacetyl chloride in a manner similar to that described in Example 53. The product is purified by chromatography on a column of 100 g of silica gel with cyclohexane-acetone (3:1) as the eluant, and subsequently reduced to the title compound using lithium aluminium hydride as the reducing agent. The compound is isolated as the hydrochloride. Yield 300 mg (16%). After recrystallization from acetone it melts at 233°–240° C.

EXAMPLE 75

2-(2-Ethoxyethyl)-2'-hydroxy-5-methyl-9-phenyl-6,7-benzomorphan hydrochloride, α-isomer The hydrobromide (2.5 g or 6.9 mmoles) of the α-isomer of 2'-hydroxy-5-methyl-9-phenyl-6,7-benzomorphan (cf. Example 52) is N-acylated with 2.57 g (21 mmoles) of ethoxyacetyl chloride in a manner similar to that described in Example 53. The product is purified by chromatography on a column of 80 g of silica gel with cyclohexaneacetone (3:1) as the eluant and subsequently reduced to the title compound with lithium aluminium hydride. The compound is isolated as the hydrochloride. Yield 1.4 g (52%). After recrystallization from methanol-ethyl acetate it melts at 213°–216° C.

EXAMPLE 76

2'-Hydroxy-2-(3-methoxypropyl)-5-methyl-9-phenyl-6,7-benzomorphan, α-isomer

The hydrobromide (2.5 g or 6.9 mmoles) of the α-isomer of 2'-hydroxy-5-methyl-9-phenyl-6,7-benzomorphan (cf. Example 52) is N-acylated with 2.57 g (21 mmoles) of 3-methoxypropionyl chloride in a manner similar to that described in Example 53. The product is purified by chromatography on a column of 80 g of silica gel with cyclohexane-acetone (3:1) as the eluant and subsequently reduced to the title compound with lithium aluminium hydride. The product is purified by chromatography on a column of 80 g silica gel with chloroform-methanol (9:1) as the eluant. After crystallization from isopropyl alcohol the m.p. is 190°–194° C. Yield 1.1 g (45%).

EXAMPLE 77

2-(3-Cyanopropyl)-2'-hydroxy-5-methyl-9-phenyl-6,7-benzomorphan hydrochloride, α-isomer In a manner similar to that described in Example 61, but using 1.5 g (4.17 mmoles) of the same starting material with 0.47 g (4.6 mmoles) of 4-chlorobutyronitrile as the alkylating agent, the title compound is obtained. This time the reaction is carried out at 70° C. (20 hours). The hydrochloride is recrystallized from methanol-ethyl acetate. Yield 0.7 g (44%), m.p. 246°–251° C. (dec).

EXAMPLE 78

5-Ethyl-2'-hydroxy-9-phenyl-6,7-benzomorphan hydrobromide, α-isomer

A solution of 7.4 g (20.7 mmoles) of 5-ethyl-2'-methoxy-2-methyl-9-phenyl-6,7-benzomorphan hydrochloride (cf. Example 22) in 200 ml of water is shaken with 10 ml of concentrated aqueous ammonia and 200 ml of chloroform. The solution of the free base in chloroform thus obtained is dried with magnesium sulphate and evaporated in vacuo. The residue is dissolved in 75 ml of ethyl chloroformate and this solution is refluxed for 4 hours. Again 50 ml of ethyl chloroformate is added and refluxing is continued for 16 hours. Then the mixture is concentrated in vacuo leaving a product which is treated with 75 ml of 47% hydrobromic acid at 90° C. for 20 hours.

Then the mixture is cooled to room temperature, when the hydrobromide of the desired product precipitates. Yield 6.85 g (88%). This hydrobromide is used as the starting material in some of the following Examples. After recrystallization from methanol-ethyl acetate it melts at 294°–303° C.

EXAMPLE 79

2,5-Diethyl-2'-hydroxy-9-phenyl-6,7-benzomorphan hydrochloride, α-isomer

In a manner similar to that described in Example 61, but using 1.2 g (3.2 mmoles) of 5-ethyl-2'-hydroxy-9-phenyl-6,7-benzomorphan hydrobromide, α-isomer (cf. Example 78), as the starting material and 0.45 g (3.5 mmoles) of ethyl bromide as the alkylating agent, the title compound is obtained. This time the reaction is carried out at 130° C. (20 hours). The hydrochloride is recrystallized from methanol-ethyl acetate. Yield 0.6 g (53%), m.p. 281°–287° C. (dec).

EXAMPLE 80

5-Ethyl-2'-hydroxy-2-(2-methoxyethyl)-9-phenyl-6,7-benzomorphan hydrochloride, α-isomer The hydrobromide (1.5 g or 4.0 mmoles) of the α-isomer of 5-ethyl-2'-hydroxy-9-phenyl-6,7-benzomorphan (cf. Example 78) is N-acylated with 1.3 g (12.0 mmoles) of methoxyacetyl chloride in a manner similar to that described in Example 53. The product is purified by chromatography on a column of 80 g of silica gel with ethyl acetate as the eluant and subsequently reduced to the title compound with lithium aluminium hydride. The compound is isolated as the hydrochloride. Yield 410 mg (25%). After recrystallization (2 times) from methanol-ethyl acetate it melts at 262°–272° C. (dec).

EXAMPLE 81

2,6-Dimethyl-9-hydroxy-2'-methoxy-9-(α-methylphenyl)-6,7-benzomorphan hydrochloride, α-isomer In a manner similar to that described in Example 5, but using o-bromotoluene instead of p-bromoanisole, a mixture of stereoisomers is obtained. The mixture of α- and β-isomers is separated by crystallization of the hydrochlorides. Yield of the α-isomer: 56%, m.p. 242°–253° C.

The β-isomer is not obtained crystalline, the yield being 2%.

EXAMPLE 82

2,5-Dimethyl-2'-methoxy-9-(o-methylphenyl)-6,7-benzomorphan hydrochloride, α-isomer In a manner similar to that described in Example 26, but using the α-isomer of 2,5-dimethyl-9-hydroxy-2'-methoxy-9-(o-methylphenyl)-6,7-benzomorphan hydrochloride (cf. Example 81) as the starting material, the title compound is obtained. The hydrochloride is recrystallized from ethyl acetate. Yield 13%, m.p. 239°–246° C. (dec).

EXAMPLE 83

2,5-Dimethyl-2'-hydroxy-9-(o-methylphenyl)-6,7-benzomorphan hydrochloride, α-isomer In a manner similar to that described in Example 29, but using the α-isomer of 2,5-dimethyl-2'-methoxy-9-(o-methylphenyl)-6,7-benzomorphan hydrochloride (cf. Example 82) as the starting material, the title compound is obtained. The hydrochloride is recrystallized from methanol-ethyl acetate. Yield 75%, m.p. 231°–238° C. (dec).

EXAMPLE 84

9-(m-Chlorophenyl)-2,5-dimethyl-9-hydroxy-2'-methoxy-6,7-benzomorphan hydrochloride, α- and β-isomers In a manner similar to that described in Example 5, but using m-bromochlorobenzene instead of p-bromoanisole, a mixure of stereoisomers is obtained which is separated in the usual way by chromatography on silica gel, the eluant being toluene-ethyl acetate (9:1). Both isomers are secured as the hydrochlorides. After recrystallization from methanol-ethyl acetate, the α-isomer melts at 250°–254° C., yield 47%, whereas the β-isomer melts at 219°–223° C., yield 8%.

EXAMPLE 85

9-Chloro-9-(m-chlorophenyl)-2,5-dimethyl-2'-methoxy-6,7-benzomorphan hydrochloride In a manner similar to that described in Example 15, but using the α-isomer of 9-(m-chlorophenyl)-2,5-dimethyl-9-hydroxy-2'-methoxy-6,7-benzomorphan hydrochloride (cf. Example 84) as the starting material, the title compound is obtained. The hydrochloride is recrystallized from methanol-ethyl acetate. Yield 73%, m.p. 230°–234° C.

EXAMPLE 86

9-(m-Chlorophenyl)-2,5-dimethyl-2'-methoxy-6,7-benzomorphan hydrochloride

In a manner similar to that described in Example 21, but using 9-chloro-9-(m-chlorophenyl)-2,5-dimethyl-2'- methoxy-6,7-benzomorphan hydrochloride (cf. Example 85) as the starting material, the title compound is obtained. This hydrochloride is used as the starting material in the following Example without any purification.

EXAMPLE 87

9-(m-Chlorophenyl)-2,5-dimethyl-2'-hydroxy-6,7-benzomorphan oxalate, α-isomer

In a manner similar to that described in Example 29, but using 9-(m-chlorophenyl)-2,5-dimethyl-2'-methoxy-6,7-benzomorphan hydrochloride (cf. Example 86) as the starting material, the title compound is obtained. The oxalate is recrystallized from acetone. Yield 25%, m.p. 232°–235° C.

EXAMPLE 88

2,5-Dimethyl-9-hydroxy-2'-methoxy-9-(m-methoxyphenyl)-6,7-benzomorphan hydrochloride, α- and β-isomers In a manner similar to that described in Example 5, but using m-bromoanisole instead of the para-isomer, a mixture of stereoisomers is obtained which is separated in the usual way by chromatography on silica gel, the eluant being toluene-ethyl acetate (1:1). Both isomers are secured as the hydrochlorides. After recrystallization from methanol-ethyl acetate, the α-isomer melts at 248°–253° C. (dec), yield 45%, whereas the β-isomer has a m.p. of 207°–210° C. (dec), yield 11%.

EXAMPLE 89

9-Chloro-2,5-dimethyl-2'-methoxy-9-(m-methoxyphenyl)-6,7-benzomorphan hydrochloride In a manner similar to that described in Example 15, but using the α-isomer of 2,5-dimethyl-9-hydroxy-2'-methoxy-9-(m-methoxyphenyl)-6,7-benzomorphan hydrochloride (cf. Example 88) as the starting material, the title compound is obtained.

The hydrochloride is recrystallized from methanol-ethyl acetate. Yield 75%, m.p. 202°–206° C.

EXAMPLE 90

2,5-Dimethyl-2'-methoxy-9-(m-methoxyphenyl)-6,7-benzomorphan hydrochloride, α isomer In a manner similar to that described in Example 21, but using 9-chloro-2,5-dimethyl-2'-methoxy-9-(m-methoxyphenyl)-6,7-benzomorphan hydrochloride (cf. Example 89) as the starting material, the title compound is obtained. The hydrochloride is recrystallized from ethyl acetate. Yield 65%, m.p. 213°–216° C.

EXAMPLE 91

2,5-Dimethyl-2'-hydroxy-9-(m-hydroxyphenyl)-6,7-benzomorphan hydrochloride, α-isomer In a manner similar to that described in Example 29, but using the α-isomer of 2,5-dimethyl-2'-methoxy-9-(m-methoxyphenyl)-6,7-benzomorphan hydrochloride (cf. Example 90) as the starting material, the title compound is obtained. The hydrochloride is recrystallized from methanol-ethyl acetate. Yield 60%, m.p. 273°–278° C.

EXAMPLE 92

2,5-Dimethyl-9-phenyl-6,7-benzomorphan hydrochloride, α-isomer

The free base of the α-isomer of 2,5-dimethyl-2'-hydroxy-9-phenyl-6,7-benzomorphan (cf. Example 27) is prepared by shaking 660 mg (2 mmoles) of the hydrochloride with chloroform and 25% of aqueous ammonia and evaporating the dried ($MgSO_4$) chloroform extract. The residue is added to a mixture of 30 ml of dry dimethylformamide, 370 mg (2.2 mmoles) of 5-chloro-1-phenyl-1H-tetrazole and 640 mg of anhydrous sodium carbonate.

This mixture is stirred and heated at 80° C. for 16 hours after which it is cooled, filtered and concentrated under reduced pressure. The residue is rubbed with 5 ml of methanol and the crystalline material, thus obtained, collected by filtration. Yield 460 mg, m.p. 195°–198° C.

This product (440 mg), being the 2'-(1-phenyl-1H-tetrazol-5-yloxy)derivative of the title compound is submitted to catalytic hydrogenolysis by shaking its solution in 10 ml of dry methanol with hydrogen at 50° C. and atmospheric pressure, the catalyst being 5% palladium on charcoal (250 mg). The absorption of hydrogen is complete within 4 hours. Removal of the catalyst by filtration and evaporation of the methanol in vacuo leaves the product which is purified by chromatography on aluminium oxide with ether as the eluant, and finally isolated as the hydrochloride (100 mg m.p. 272°–274° C.).

EXAMPLE 93

(+) and (−) 2,5-Dimethyl-2'-hydroxy-9-phenyl-6,7-benzomorphan, α-isomers

To 30 ml of a hot aqueous solution of 990 mg (3 mmoles) of the hydrochloride of the α-isomer of 2,5-dimethyl-2'-hydroxy-9-phenyl-6,7-benzomorphan, obtained according to Example 27, there is added 984 mg (3 mmoles) of ammonium L(−)-3-bromocamphor-8-sulphonate dissolved in 20 ml of hot water. The mixture is allowed to cool to room temperature when 1.63 g of a white crystalline salt separates. After recrystallization from 75 ml of ethanol, 580 mg of a salt is obtained melting at 276°–279° C., the optical rotation being $[\alpha]_D^{26} = -72°$ (2% in DMF).

By shaking with chloroform and 25% aqueous ammonia, the salt is decomposed and the free base is secured by evaporation of the dried chloroform extract. It is a crystalline substance (m.p. 242°–245° C.) showing an optical rotation of $[\alpha]_D^{26} = +22°$ (2% in DMF). The hydrochloride of this (+) enantiomer melts at 247°–251° C. and has an optical rotatory power of $[E]_D^{26} = +15°$ (2% in methanol). The combined mother liquors are evaporated and the residue is shaken with chloroform and 25% aqueous ammonia to collect the remaining part of the compound as a free base, now consisting mainly of the laevo rotatory enantiomer. This base is converted to the hydrochloride (407 mg) which is dissolved in 40 ml of hot water containing 456 mg of ammonium d(+)-3-bromocamphor-8-sulphonate. After cooling, 570 mg of crystalline material separates, which after recrystallization from ethanol melts at 277°–279° C. Yield 300 mg. $[\alpha]_D^{26} = +72°$ (2% in DMF). The free base melts at 241°–245° C., $[\alpha]_D^{26} = -20°$ (2% in DMF), whereas the hydrochloride shows $[\alpha]_D^{26} = -14.5°$ (2% in methanol) with m.p. 248°–252° C.

EXAMPLE 94

9-Chloro-2,5-dimethyl-2'-hydroxy-9-phenyl-6,7-benzomorphan hydrochloride

In a manner similar to that described in Example 15, but using 346 mg (1 mmole) of the hydrochloride of the β-isomer of 2',9-dihydroxy-5-methyl-9-phenyl-6,7-benzomorphan (cf. Example 42) as the starting material, the above compound is obtained as the hydrochloride. It is recrystallized from methanol-ethyl acetate. Yield 70%, m.p. 215°–222° C. (dec).

EXAMPLE 95

2,5-Dimethyl-2'-hydroxy-9-phenyl-6,7-benzomorphan hydrochloride, α-isomer

In a manner similar to that described in Example 21, but using 182 mg (0.5 mmole) of the hydrochloride of 9-chloro-2,5-dimethyl-2'-hydroxy-9-phenyl-6,7-benzomorphan (cf. Example 94) as the starting material, a mixture of the α- and β-isomers in a proportion of 19:1 of the above compound is obtained. This mixture is converted into the hydrochlorides, which after recrystallization from methanol-ethyl acetate yields 112 mg (70%) of the hydrochloride of the α-isomer. It is identical with the product obtained in Example 27.

EXAMPLE 96

9-Chloro-2,5-dimethyl-2'-hydroxy-9-phenyl-6,7-benzomorphan hydrochloride

In a manner similar to that described in Example 41, but using 1.4 g (4 mmoles) of 9-chloro-2,5-dimethy-2'-methoxy-9-phenyl-6,7-benzomorphan (cf. Example 15) the above compound is obtained in a yield of 80%. It is identical with the product obtained in Example 95.

EXAMPLE 97

2'-Hydroxy-2-(2-hydroxy-2-methylpropyl)-5-methyl-9-phenyl-6,7-benzomorphan hydrochloride, α-isomer The free base (1.84 g) of the α-isomer of 2'-hydroxy-5-methyl-9-phenyl-6,7-benzomorphan is made from 1.5 g (7.0 mmoles) of the hydrobromide (cf. Example 52) by shaking with chloroform and 25% of aqueous ammonia followed by evaporation of the dried (MgSO₄) chloroform extract. The residue is dissolved in 20 mg of methanol. Isobutyleneoxyde (1.2 ml, 13.5 mmoles) is added and the mixture is then heated for 5 hours at 100° C. in a glass pressure vessel. The reaction product is obtained by evaporation of the mixture in vacuo, whereafter the basic product which is left is converted into its hydrochloride by the addition of hydrogen chloride dissolved in isopropanol. The salt is recrystallized from methanol-ethyl acetate. Yield 65%, m.p. 250° C. (dec).

Compositions

The following Examples in which the α-isomer of 2,5-dimethyl-2'-hydroxy-9-phenyl-6,7-benzomorphan or a salt thereof is used as the active compound, are illustrative of the compositions of the invention.

The above compound is hereinafter referred to as "the active compound".

EXAMPLE 98

Tablet formulation

|  | per tablet, mg. |
|---|---|
| HCl salt of the active compound | 1.5 |
| Indigotinelake | 0.2 |
| Magnesium stearate | 0.5 |
| Microcrystalline cellulose | 97.8 |

EXAMPLE 99

Tablet formulation

|  | per tablet, mg. |
|---|---|
| HCl salt of the active compound | 1.0 |
| Lactose, U.S.P. | 50.0 |
| Starch, U.S.P. | 43.0 |
| Pregelatinated starch (Snowflake$^R$) | 2.5 |
| Silicium oxide (Aerosil 200$^R$) | 2.5 |
| Magnesium stearate | 1.0 |

EXAMPLE 100

Capsule formulation

|  | per capsule, mg. |
|---|---|
| HCl salt of the active compound | 0.5 |
| Starch, U.S.P. | 15.0 |
| Lactose, U.S.P. | 157.5 |
| Magnesium stearate | 2.0 |

The mixture is filled into no. 4 hard shell gelatin capsules.

EXAMPLE 101

Capsule formulation 0.1–10% of the active compound or a pharmaceutically acceptable salt thereof in excipient. Filling material (100 mg) in Scherer soft gelatin capsule no. 2.

EXAMPLE 102

Suppository formulation

|  | per suppository, mg. |
|---|---|
| Lactic acid salt of the active compound | 2 |
| Lactose, U.S.P. | 20 |
| Estarine B$^R$ | 1978 |

EXAMPLE 103

Suppository formulation 0.01–1% of the active compound or a pharmaceutically acceptable salt thereof in excipient. Filling material (1000 mg) in Scherer soft gelatin suppository no. 17.

EXAMPLE 104

Injectable formulation

|  | per ml, mg. |
|---|---|
| HCl salt of the active compound | 2.5 |
| Sodium chloride | 8.5 |
| Sodium metabisulphite | 1.0 |

|  | per ml, mg. |
|---|---|
| Water for injection | ad 1.0 ml |

EXAMPLE 105

Injectable formulation

|  | per ml, mg. |
|---|---|
| Lactic acid salt of the active compound | 10.0 |
| Lactic acid | 8.0 |
| Sodium hydroxide | ad pH 5.0 |
| Water for injection | ad 1.0 ml |

Tests were conducted with respect to the pharmacological properties of various 6,7-benzomorphans according to this invention which are included within general formula I above, and in which the substituents R, $R_1$ and $R_2$ are as indicated in the below Table A.

The tests conducted were as follows:

Tail Withdrawal Test In Rats

The analgesic potency of the tested compounds was determined by the so-called tail withdrawal test in rats having a body weight of $200\pm30$ g substantially in accordance with the standard procedures described by Janssen P. A. J., Niemegeers C. J. E. and Dony J. G. H.; Arzneim-Forsch, 13, 502 (1963). The test procedure was substantially as described, with the exceptions that measurements were made more frequently, the cut-off time was reduced from 15 seconds to 10 seconds, and the results were rated according to three different levels of analgesia, defined as follows:

a. Moderate analgesia (M.A. on Table A)—the tail withdrawal reaction time is $>6$ and $<10$ seconds.
b. Pronounced analgesia (P.A. on Table A)—no tail withdrawal response over a reaction time $>10$ seconds, but slight movements of the tail in the warm water cup.
c. Surgical analgesia (S.A. on Table A)—no tail withdrawal response over a reaction time $>10$ seconds, and no movements or reaction of the tail.

Table A gives the dosages, in mg./kg of body weight, administered subcutaneously that constitute the $ED_{50}$-values for each of the defined compounds to achieve the above defined levels of analgesia (M.A., P.A. and S.A.). For purposes of comparison, Table A also gives the corresponding values for Nalorphine and Pentazocine.

Narcotic antagonist Activity In Rats

In order to test the (narcotic antagonist) activity of the tested compounds, that is, the potency of such compounds in reversing the respiratory depression, loss of righting reflex, muscular rigidity and surgical analgesia resulting from the administration of a high dose of fentanyl. Wistar rats were given a subcutaneous injection of 0.63 mg/kg body weight of fentanyl to induce the described phenomena. 30 minutes after the fentanyl dose, the same animals received an intravenous injection of the identified test compounds or of nalorphine or pentazocine for comparative purposes. $ED_{50}$-values were calculated for antagonism of each of the four parameters, the mean of these values being used.

Writhing Test In Rats

Femal Wistar rats (150–190 g) were injected with 1 ml of a 1%-solution of acetic acid I.P. and the number of writhes were noted during the 25 minutes following the injection. The various test compounds identified in Table A, and also nalorphine and pentazocine for the purposes of comparison, were administered subcutaneously 30 minutes, or orally 45 minutes piror to the standard injection of acetic acid.

The test compounds were dissolved in distilled water.

Table A gives, for each test compound, the $ED_{50}$ in mg/kg, this being the dose of compound required to reduce the writhing score to 50% of that obtained for a vehicle treated control group tested on the same day.

TABLE A

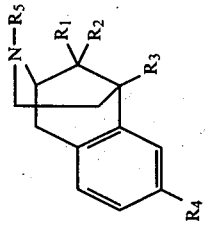

| $R_1$ | $R_2$ | $R_3$ | $R_4$ | $R_5$ | $\alpha_D$ | isomer | base salt | Tail Withdrawal Test M.A. | P.A. | S.A. | Nalorphine like activity | Writhing Test s.c. | p.o. |
|---|---|---|---|---|---|---|---|---|---|---|---|---|---|
| $C_6H_5$ | OH | $CH_3$ | OH | $CH_3$ | ± | β | HCl | >2.2 | >2.2 | >2.2 | >2.2 | >3.2 | >32 |
| $C_6H_5$ | $OCH_3$ | $CH_3$ | OH | $CH_3$ | ± | β | $(COOH)_2$ | >2.2 | >2.2 | >2.2 | 1.47 | >3.2 | >32 |
| $C_6H_5$ | $OC_2H_5$ | $CH_3$ | OH | $CH_3$ | ± | β | $(COOH)_2$ | >2.2 | >2.2 | >2.2 | 1.36 | >3.2 | >32 |
| $C_6H_5$ | OH | $CH_3$ | OH | $CH_3$ | ± | α | HCl | >2.2 | >2.2 | >2.2 | ~2.2 | >3.2 | >32 |
| $C_6H_5$ | $OCH_3$ | $CH_3$ | OH | $CH_3$ | ± | α | $(COOH)_2$ | >2.2 | >2.2 | >2.2 | 0.62 | 2.48 | >32 |
| $C_6H_5$ | $OC_2H_5$ | $CH_3$ | OH | $CH_3$ | ± | α | $(COOH)_2$ | >2.2 | >2.2 | >2.2 | >2.2 | 21.2 | 29.1 |
| $C_6H_5$ | $OC_3H_7$ | $CH_3$ | OH | $CH_3$ | ± | α | $(COOH)_2$ | >2.2 | >2.2 | >2.2 | >2.2 | >3.2 | >32 |
| $C_6H_5$ | $OC(O)CH_3$ | $CH_3$ | OH | $CH_3$ | ± | α | HCl | >2.2 | >2.2 | >2.2 | 0.39 | >3.2 | >32 |
| $C_6H_5$ | Cl | $CH_3$ | OH | $CH_3$ | ± | β | $(COOH)_2$ | >2.2 | >2.2 | >2.2 | >2.2 | >3.2 | >32 |
| $C_6H_5$ | H | $CH_3$ | OH | $CH_3$ | ± | α | HCl | 1.6 | >2.2 | >2.2 | 0.87 | 0.75 | 1.15 |
| $C_6H_5$ | H | $CH_3$ | OH | $CH_3$ | + | α | HCl | >2.2 | >2.2 | >2.2 | 0.32 | 0.65 | |
| $C_6H_5$ | H | $CH_3$ | OH | $CH_3$ | − | α | HCl | >2.2 | >2.2 | >2.2 | >2.2 | >3.2 | |
| $C_6H_5$ | H | $CH_3$ | $OCH_3$ | $CH_3$ | ±a | HCl >2.2 | | >2.2 | >2.2 | >2.2 | 1.88 | 1.80 | 2.23 |
| $C_6H_5$ | H | $C_2H_5$ | OH | $CH_3$ | ± | β | HCl | >2.2 | >2.2 | >2.2 | ~3.2 | >3.2 | >32 |
| $C_6H_5$ | H | $C_2H_5$ | OH | $CH_3$ | ± | α | HCl | >2.2 | >2.2 | >2.2 | 0.77 | 0.52 | 1.32 |
| $C_6H_5$ | H | $C_2H_5$ | $OCH_3$ | $CH_3$ | ± | α | HCl | >2.2 | >2.2 | >2.2 | 0.82 | ~3.2 | 4.6 |
| $C_6H_5$ | H | $C_3H_7$ | OH | $CH_3$ | ± | α | HCl | >2.2 | >2.2 | >2.2 | >2.2 | 1.23 | 5.0 |
| $C_6H_5$ | H | $C_3H_7$ | $OCH_3$ | $CH_3$ | ± | α | HCl | >2.2 | >2.2 | >2.2 | 1.51 | 9.2 | 5.1 |
| $C_6H_5$ | H | $-CH_2CH=CH_2$ | OH | $CH_3$ | ± | α | HCl | >2.2 | >2.2 | >2.2 | >2.2 | 0.32 | 13.7 |
| $C_6H_5$ | H | $-CH_2CH=CH_2$ | OH | $CH_3$ | ± | α | HCl | >2.2 | >2.2 | >2.2 | >2.2 | >3.2 | >32 |
| $C_6H_5$ | OH | $CH_3$ | OH | $CH_3$ | ± | α | HCl | >2.2 | >2.2 | >2.2 | 0.50 | >3.2 | >32 |
| $C_6H_5$ | H | $CH_3$ | OH | H | ± | α | HCl | >2.2 | >2.2 | >2.2 | >2.2 | >3.2 | >32 |
| $C_6H_5$ | H | $CH_3$ | OH | $C_2H_5$ | ± | α | HCl | >2.2 | >2.2 | >2.2 | 1.11 | 3.8 | 4.4 |
| $C_6H_5$ | H | $CH_3$ | OH | $n-C_3H_7$ | ± | α | HCl | >2.2 | >2.2 | >2.2 | 0.45 | >3.2 | >32 |
| $C_6H_5$ | H | $CH_3$ | OH | $n-C_4H_9$ | ± | α | HCl | >2.2 | >2.2 | >2.2 | 0.41 | ~3.2 | 17.9 |
| $C_6H_5$ | H | $CH_3$ | OH | $n-C_6H_{13}$ | ± | α | HCl | >2.2 | >2.2 | >2.2 | 1.35 | >3.2 | >32 |
| $C_6H_5$ | H | $CH_3$ | OH | $CH_2-CH=CH_2$ | ± | α | HCl | >2.2 | >2.2 | >2.2 | 0.29 | 2.9 | 20.6 |
| $C_6H_5$ | H | $CH_3$ | OH | $-CH_2-CH=C(CH_3)_2$ | ± | α | HCl | >2.2 | >2.2 | >2.2 | 0.88 | >3.2 | >32 |
| $C_6H_5$ | H | $CH_3$ | OH | $-CH_2-C\equiv CH$ | ± | α | HCl | >2.2 | >2.2 | >2.2 | >2.2 | >3.2 | >32 |
| $C_6H_5$ | H | $CH_3$ | OH | $-CH_2-\triangle$ | ± | α | HCl | >2.2 | >2.2 | >2.2 | 0.048 | 2.0 | 26.9 |
| $C_6H_5$ | H | $CH_3$ | OH | $-CH_2-\square$ | ± | α | HCl | >2.2 | >2.2 | >2.2 | 0.31 | >3.2 | >32 |

TABLE A-continued

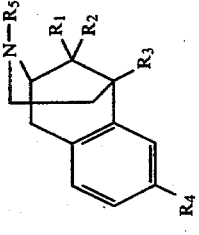

| R₁ | R₂ | R₃ | R₄ | R₅ | $\alpha_D$ | isomer | base salt | Tail Withdrawal Test M.A. | P.A. | S.A. | Nalorphine like activity | Writhing Test s.c. | p.o. |
|---|---|---|---|---|---|---|---|---|---|---|---|---|---|
| C₆H₅ | H | CH₃ | OH | cyclopentyl-CH₃ | ± | α | HCl | >2.2 | >2.2 | >2.2 | 0.31 | >3.2 | >32 |
| C₆H₅ | H | CH₃ | OH | cyclohexenyl-CH₂ | ± | α | HCl | >2.2 | >2.2 | >2.2 | >2.2 | 1.2 | ~36 |
| C₆H₅ | H | CH₃ | OH | CH₂CH₂OCH₃ | ± | α | HCl | >2.2 | >2.2 | >2.2 | 0.11 | 0.67 | 5.2 |
| C₆H₅ | H | CH₃ | OH | CH₂CH₂OC₂H₅ | ± | α | HCl | >2.2 | >2.2 | >2.2 | 0.51 | 0.95 | 15.7 |
| C₆H₅ | H | CH₃ | OH | CH₂CH₂CH₂OCH₃ | α | α | — | >2.2 | >2.2 | >2.2 | 0.38 | 1.1 | >32 |
| C₆H₅ | H | CH₃ | OH | (CH₂)₃—C≡N | ± | α | HCl | >2.2 | >2.2 | 1.2 | ~3.2 | >32 | |
| C₆H₅ | H | CH₃ | OH | CH₂CH₂C₆H₅ | ± | α | HCl | >2.2 | >2.2 | >2.2 | 1.6 | 0.68 | 12.3 |
| C₆H₅ | H | CH₃ | OH | γ—CH₂CH₂C₆H₄OCH₃ | 35 | α | HCl | >2.2 | >2.2 | >2.2 | 0.75 | 2.63 | 3.8 |
| C₆H₅ | H | CH₃ | OH | | | α | | | | | 0.89 | >3.2 | ~32 |
| C₆H₅ | H | CH₃ | OH | tetrahydrofuranyl-CH₂ | ± | α | HCl | 1.5 | >2.2 | >2.2 | 0.061 | 0.33 | 29.8 |
| C₆H₅ | H | C₂H₅ | OH | C₂H₅ | ± | α | HCl | >2.2 | >2.2 | >2.2 | 1.25 | >3.2 | 12.3 |
| C₆H₅ | H | C₂H₅ | OH | CH₂CH₂OCH₃ | ± | α | HCl | 1.9 | >2.2 | >2.2 | 0.17 | 0.38 | 6.7 |
| 2-C₆H₄CH₃ | H | CH₃ | OH | CH₃ | ± | α | (COOH)₂ | >2.2 | >2.2 | >2.2 | >2.2 | 0.42 | 3.4 |
| 4-C₆H₄CH₃ | H | CH₃ | OH | CH₃ | ± | α | (COOH)₂ | >2.2 | >2.2 | >2.2 | 1.59 | 3.33 | >32 |
| 3-C₆H₄Cl | H | CH₃ | H | CH₃ | ± | α | HCl | >2.2 | >2.2 | >2.2 | >2.2 | ~3.2 | 16.2 |
| 3-C₆H₄OH | H | CH₃ | H | CH₃ | ± | α | HCl | >2.2 | >2.2 | >2.2 | >2.2 | 1.2 | >32 |
| 3-C₅H₄N | H | CH₃ | OH | CH₃ | ± | α | HCl | >2.2 | >2.2 | >2.2 | 0.16 | >3.2 | >32 |
| Nalorphine | | | | | | | | 28 | >22 | >22 | 2.2 | 6.6 | 278 |
| Pentazocine | | | | | | | | 14.7 | 53 | >100 | | 5.6 | |

What we claim is:

1. A benzomorphan compound of the formula

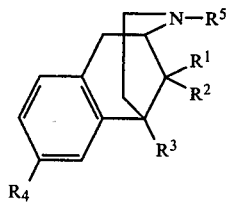

or a pharmaceutically acceptable salt thereof wherein $R^1$ is unsubstituted phenyl or phenyl substituted by a substituent selected from the group consisting of halogen, lower alkyl, trifluoromethyl, hydroxy, lower alkoxy, di(lower) alkylamino, and piperidino; $R^2$ is hydrogen, halogen, hydroxy, lower alkoxy, or acetoxy; $R^3$ is alkyl or alkenyl having up to four carbon atoms; $R^4$ is hydrogen, hydroxy, lower alkoxy, lower alkanoyloxy, nicotinoyloxy, or phenylloweralkanoyloxy; and $R^5$ is loweralkyl or, when $R^2$ is hydrogen and is trans to $R^3$, $R^5$ is hydrogen, loweralkyl or loweralkenyl, propargyl, lowercycloalkyl being unsubstituted or substituted by one or two lower alkyl groups, lowercycloalkylloweralkyl wherein the lowercycloalkyl group is unsubstituted or substituted by one or two lower alkyl groups, lowercycloalkenylloweralkyl, cyanoloweralkyl, hydroxyloweralkyl, loweralkoxyloweralkyl, or phenylloweralkyl wherein the phenyl group is unsubstituted or substituted by lower alkoxy, halogen, or nitro.

2. A compound or salt as in claim 1 wherein $R^1$ and $R^3$ are cis to one another.

3. A compound or salt as in claim 2 wherein $R^1$ is phenyl, $R^2$ is hydrogen, and $R^4$ is hydroxy or methoxy.

4. A compound or salt as in claim 2 wherein $R^1$ is phenyl, $R^2$ is hydrogen, $R^3$ is alkyl, and $R^4$ is hydroxy or methoxy.

5. A compound or salt as in claim 2 wherein $R^1$ is phenyl, $R^2$ is hydrogen, $R^3$ is alkyl, $R^4$ is hydroxy or methoxy, and $R^5$ is methyl.

6. A compound or salt as in claim 2 wherein $R^1$ is phenyl, $R^2$ is hydrogen, $R^3$ is methyl, $R^4$ is hydroxy, and $R^5$ is methyl.

7. The (+)-enantiomer of a compound or salt as claimed in claim 6.

8. A compound or salt as in claim 2 wherein $R^1$ is phenyl, $R^2$ is hydrogen, $R^3$ is ethyl, n-propyl or allyl, $R^4$ is hydroxy, and $R^5$ is methyl.

9. A compound or salt as in claim 2 wherein $R^1$ is phenyl, $R^2$ is hydrogen, $R^3$ is methyl, ethyl or n-propyl, $R^4$ is methoxy, and $R^5$ is methyl.

10. A compound or salt as in claim 2 wherein $R^1$ is o-tolyl or m-hydroxyphenyl, $R^2$ is hydrogen, $R^3$ is methyl, $R^4$ is hydroxy, and $R^5$ is methyl.

11. A compound or salt as in claim 1 wherein $R^1$ is phenyl, $R^2$ is hydrogen, $R^3$ is methyl, $R^4$ is hydroxy, and $R^5$ is ethyl, methoxyethyl, ethoxyethyl, or p-methoxyphenethyl.

12. A compound or salt as in claim 1 wherein $R^1$ is phenyl, $R^2$ is hydrogen, $R^3$ is methyl, $R^4$ is hydroxy and $R^5$ is, phenethyl, allyl, n-butyl, cyclopropylmethyl, or methoxypropyl.

13. A compound or salt as in claim 1 wherein $R^1$ is phenyl, $R^2$ is hydrogen, $R^3$ is methyl, $R^4$ is hydroxy, and $R^5$ is hydroxyloweralkyl.

14. A compound or salt as in claim 1 wherein $R^1$ is phenyl, $R^2$ is hydrogen, $R^3$ is methyl, $R^4$ is hydroxy, and $R^5$ is 2-hydroxy-2-methylpropyl.

15. A compound or salt as in claim 1 wherein $R^1$ is phenyl, $R^2$ is hydrogen, $R^3$ is ethyl, $R^4$ is hydroxy, and $R^5$ is ethyl or methoxyethyl.

16. A compound or salt as in claim 1 wherein $R^1$ is phenyl, $R^2$ is hydroxy, $R^3$ is methyl or ethyl, $R^4$ is hydroxy or methoxy, and $R^5$ is methyl.

17. A compound or salt as in claim 1 wherein $R^1$ is phenyl, $R^2$ is chlorine, $R^3$ is methyl or ethyl, $R^4$ is hydroxy or methoxy, and $R^5$ is methyl.

18. A compound or salt as in claim 1 wherein $R^1$ is phenyl, $R^2$ is hydrogen, $R^3$ is methyl or ethyl, $R^4$ is hydroxy or methoxy, and $R^5$ is hydrogen.

19. A pharmaceutical composition with analgesic and/or morphine-antagonistic activity comprising an effective analgesic and/or morphine-antagonistic amount of a compound or salt as in claim 1 and a pharmaceutically acceptable diluent or carrier therefor.

20. The method of raising the pain threshold and/or counteracting the physiological effects of an opiate in a warm-blooded animal, which comprises administering to said animal an effective analgesic and/or morphine-antagonistic amount of a compound or salt as in claim 1.

21. A benzomorphan compound of the formula

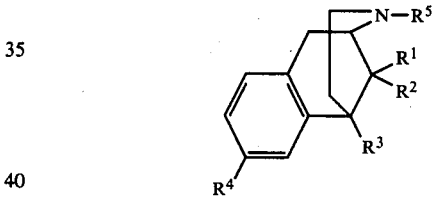

or a pharmaceutically acceptable salt thereof wherein $R^1$ is unsubstituted phenyl or phenyl substituted by a substituent selected from the group consisting of halogen, methyl, trifluoromethyl, hydroxy, methoxy, dimethylamino, and piperidino; $R^2$ is hydrogen, halogen, hydroxy, alkoxy having up to three carbon atoms, or acetoxy; $R^3$ is alkyl or alkenyl having up to four carbon atoms; $R^4$ is hydrogen, hydroxy, alkoxy having up to three carbon atoms, loweralkanoyloxy, or nicotinoyloxy; $R^5$ is alkyl having up to six carbon atoms or, when $R^2$ is hydrogen and is trans to $R^3$, $R^5$ is hydrogen, alkyl having up to six carbon atoms, alkenyl having up to five carbon atoms, propargyl, cycloalkyl having up to five carbon atoms, cycloalkylalkyl having up to five carbon atoms, cycloalkenylalkyl having up to seven carbon atoms, cyanoalkyl having up to three carbon atoms in the alkyl portion thereof, hydroxyalkyl having up to four carbon atoms, alkoxyalkyl having up to five carbon atoms, or phenylalkyl having up to eight carbon atoms wherein the phenyl group is unsubstituted or substituted by methoxy, halogen, or nitro.

* * * * *

UNITED STATES PATENT AND TRADEMARK OFFICE
CERTIFICATE OF CORRECTION

PATENT NO. : 4,234,591
DATED : November 18, 1980
INVENTOR(S) : Antony M. Akkerman et al.

It is certified that error appears in the above-identified patent and that said Letters Patent are hereby corrected as shown below:

Column 16, lines 47-49, replace entire lines by

--In the following descrip- --.

Signed and Sealed this

Fourteenth Day of July 1981

[SEAL]

Attest:

Attesting Officer

GERALD J. MOSSINGHOFF

Commissioner of Patents and Trademarks